US009192414B2

(12) United States Patent
Haas et al.

(10) Patent No.: US 9,192,414 B2
(45) Date of Patent: Nov. 24, 2015

(54) IMPLANT FOR STABILIZING SPINOUS PROCESSES

(71) Applicant: Aesculap AG, Tuttlingen (DE)

(72) Inventors: Alexander Haas, Donaueschingen (DE); Claudia Stoerk, Emmingen (DE); Jens Beger, Tuttlingen (DE); Andrea Wiegele, Tuttlingen (DE); Rolando Garcia, Golden Beach, FL (US)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 14/535,436

(22) Filed: Nov. 7, 2014

(65) Prior Publication Data

US 2015/0066086 A1    Mar. 5, 2015

Related U.S. Application Data

(63) Continuation of application No. PCT/EP2013/059722, filed on May 10, 2013.

(60) Provisional application No. 61/645,716, filed on May 11, 2012.

(51) Int. Cl.
*A61B 17/70*    (2006.01)

(52) U.S. Cl.
CPC ......... *A61B 17/7067* (2013.01); *A61B 17/7062* (2013.01); *A61B 17/7068* (2013.01)

(58) Field of Classification Search
CPC .............. A61F 2/4405; A61B 17/7062; A61B 17/7067; A61B 17/7068; A61B 17/707; A61B 17/7065
See application file for complete search history.

(56) References Cited

U.S. PATENT DOCUMENTS 3,648,691 A    3/1972    Lumb
5,351,792 A    10/1994    Cohen
(Continued)

FOREIGN PATENT DOCUMENTS

DE    4411974    10/1995
DE    69431348    5/2003
(Continued)

OTHER PUBLICATIONS

Search Report and Written Opinion issued in related International Application No. PCT/EP2013/059722, dated Aug. 16, 2013.
(Continued)

*Primary Examiner* — Eduardo C Robert
*Assistant Examiner* — Julianna N Harvey
(74) *Attorney, Agent, or Firm* — RatnerPrestia

(57) ABSTRACT

An implant for stabilizing spinous processes of adjacent vertebral bodies can include first and second contact elements. The first contact element is placed onto a first side of the spinous processes and the second contact element is placed onto a second side of the spinous processes. The implant includes at least one clamping element which couples to the first contact element, can be moved relative to the second contact element, and extends through the intervertebral space between the spinous processes and the second contact element. The implant also includes at least one fixing element on the second contact element which can be brought into engagement with the at least one clamping element to clamp the second contact element in the direction of the first contact element along the at least one clamping element. The first contact element is movable relative to the at least one clamping element.

17 Claims, 14 Drawing Sheets

(56) References Cited

U.S. PATENT DOCUMENTS

| | | |
|---|---|---|
| 5,645,589 A | 7/1997 | Li |
| 6,214,050 B1 | 4/2001 | Huene |
| 6,322,883 B1 | 11/2001 | Williams |
| 6,332,883 B1 | 12/2001 | Zucherman |
| 7,048,736 B2 | 5/2006 | Robinson |
| 7,585,313 B2 | 9/2009 | Kwak |
| 7,585,316 B2 | 9/2009 | Trieu |
| 7,588,592 B2 | 9/2009 | Winslow |
| 7,727,233 B2 | 6/2010 | Blackwell |
| 7,811,307 B2 | 10/2010 | Deneuvillers |
| 8,012,207 B2 | 9/2011 | Kim |
| 8,048,120 B1 | 11/2011 | Fallin et al. |
| 8,128,659 B2 | 3/2012 | Ginsberg |
| 8,262,697 B2 | 9/2012 | Kirschman |
| 8,313,512 B2 | 11/2012 | Kwak |
| 8,343,190 B1* | 1/2013 | Mueller et al. ........ 606/248 |
| 8,361,116 B2 | 1/2013 | Edmond |
| 2003/0040746 A1* | 2/2003 | Mitchell et al. ........ 606/61 |
| 2003/0216736 A1* | 11/2003 | Robinson et al. ........ 606/61 |
| 2005/0033434 A1 | 2/2005 | Berry |
| 2005/0055031 A1 | 3/2005 | Lim |
| 2006/0084985 A1 | 4/2006 | Kim |
| 2006/0122611 A1 | 6/2006 | Morales |
| 2006/0247640 A1 | 11/2006 | Blackwell et al. |
| 2007/0032790 A1 | 2/2007 | Aschmann |
| 2007/0225706 A1* | 9/2007 | Clark et al. ........ 606/61 |
| 2007/0225724 A1 | 9/2007 | Edmond |
| 2007/0225807 A1 | 9/2007 | Phan |
| 2007/0233074 A1 | 10/2007 | Anderson |
| 2007/0270812 A1* | 11/2007 | Peckham ........ 606/61 |
| 2007/0270840 A1 | 11/2007 | Chin |
| 2007/0270856 A1* | 11/2007 | Morales et al. ........ 606/72 |
| 2008/0027438 A1 | 1/2008 | Abdou |
| 2008/0086212 A1 | 4/2008 | Zucherman |
| 2008/0108990 A1 | 5/2008 | Mitchell |
| 2008/0109082 A1 | 5/2008 | Fink |
| 2008/0109802 A1 | 5/2008 | Carrigan |
| 2008/0114367 A1 | 5/2008 | Meyer |
| 2008/0183211 A1* | 7/2008 | Lamborne et al. ........ 606/249 |
| 2008/0183218 A1* | 7/2008 | Mueller et al. ........ 606/280 |
| 2008/0228225 A1 | 9/2008 | Trautwein |
| 2008/0249569 A1 | 10/2008 | Waugh |
| 2008/0281359 A1 | 11/2008 | Abdou |
| 2008/0281360 A1 | 11/2008 | Vittur |
| 2008/0300601 A1 | 12/2008 | Fabian |
| 2008/0306488 A1 | 12/2008 | Altarac |
| 2009/0018658 A1 | 1/2009 | Garcia |
| 2009/0138055 A1 | 5/2009 | Altarac |
| 2009/0149886 A1 | 6/2009 | Zentes |
| 2009/0264927 A1* | 10/2009 | Ginsberg et al. ........ 606/246 |
| 2009/0265006 A1 | 10/2009 | Seifert |
| 2009/0292316 A1 | 11/2009 | Hess |
| 2009/0326581 A1 | 12/2009 | Galley |
| 2010/0004688 A1 | 1/2010 | Maas |
| 2010/0036419 A1* | 2/2010 | Patel et al. ........ 606/249 |
| 2010/0131009 A1 | 5/2010 | Roebling |
| 2010/0198245 A1 | 8/2010 | Haas |
| 2011/0009904 A1 | 1/2011 | Froehlich |
| 2011/0022090 A1* | 1/2011 | Gordon et al. ........ 606/249 |
| 2011/0054531 A1 | 3/2011 | Lamborne |
| 2011/0160772 A1 | 6/2011 | Arcenio |
| 2011/0160773 A1 | 6/2011 | Aschmann |
| 2011/0172711 A1* | 7/2011 | Kirschman ........ 606/252 |
| 2012/0089184 A1* | 4/2012 | Yeh ........ 606/248 |
| 2012/0101528 A1* | 4/2012 | Souza et al. ........ 606/249 |
| 2012/0109203 A1* | 5/2012 | Dryer et al. ........ 606/249 |
| 2012/0136390 A1* | 5/2012 | Butler et al. ........ 606/248 |
| 2012/0150228 A1 | 6/2012 | Zappacosta |
| 2012/0215261 A1 | 8/2012 | Massoudi |
| 2012/0221050 A1* | 8/2012 | Ingalhalikar et al. ........ 606/248 |
| 2012/0277796 A1 | 11/2012 | Gabelberger |
| 2012/0290008 A1 | 11/2012 | Kirschman |
| 2013/0066374 A1 | 3/2013 | Galley |
| 2013/0184751 A1* | 7/2013 | Siegfried ........ 606/248 |
| 2013/0184753 A1 | 7/2013 | Keiper |

FOREIGN PATENT DOCUMENTS

| | | |
|---|---|---|
| DE | 10326690 | 1/2005 |
| DE | 69828711 | 1/2006 |
| DE | 102004047566 | 5/2006 |
| DE | 102004063996 | 8/2006 |
| DE | 202006018978 | 3/2007 |
| DE | 102006021025 | 1/2008 |
| DE | 202008009344 | 10/2008 |
| DE | 202009001321 | 2/2009 |
| DE | 102007052799 | 5/2009 |
| EP | 0683653 | 9/2002 |
| EP | 1297792 | 4/2003 |
| EP | 2323574 | 2/2012 |
| GB | 2436292 | 9/2007 |
| WO | 2006102428 | 9/2006 |
| WO | 2006111174 | 10/2006 |
| WO | WO 2006/119235 A1 | 11/2006 |
| WO | 2007007819 | 6/2007 |
| WO | 2007070819 | 6/2007 |
| WO | 2007127689 | 11/2007 |
| WO | 2009127041 | 10/2009 |
| WO | 2010016949 | 2/2010 |
| WO | 2010019783 | 2/2010 |
| WO | 2010114925 | 10/2010 |
| WO | WO 2011/031924 A2 | 3/2011 |
| WO | 2012035275 | 3/2012 |
| WO | WO 2012/062889 A1 | 5/2012 |

OTHER PUBLICATIONS

Entire patent prosecution history of U.S. Appl. No. 12/372,033, filed Feb. 17, 2009, entitled, "Implant for Mutual Support of the Spinous Processes of Vertebral Bodies."
Entire patent prosecution history of U.S. Appl. No. 13/558,724, filed Jul. 26, 2012, entitled, "Surgical Apparatus."
Entire patent prosecution history of U.S. Appl. No. 13/558,789, filed Jul. 26, 2012, entitled, "Implant for Mutually Supporting the Spinous Processes of Adjacent Vertebral Bodies and a Surgical System."
Entire patent prosecution history of U.S. Appl. No. 13/891,378, filed May 10, 2013, entitled, "Surgical Fixation System, Spacer Element for a Surgical Fixation System, Use of an Implant and Method for Stabilizing Spinous Processes."
International Search Report for Application No. PCT/EP2009/004844 dated Jan. 27, 2011.
International Search Report for PCT/EP2011/069895 mailed Feb. 15, 2012.
International Search Report of International Application No. PCT/EP2009/004844. Search completed Oct. 28, 2009 (w/English language form PCT/ISA/210 to show relevance.
Notice of Allowance for U.S. Appl. No. 12/372,033, dated Mar. 6, 2012.
Notice of Allowance for U.S. Appl. No. 13/558,724, dated Dec. 11, 2014.
Office Action for U.S. Appl. No. 13/372,033, dated Nov. 8, 2011.
Office Action for U.S. Appl. No. 13/558,724, dated Oct. 7, 2014.
Office Action for U.S. Appl. No. 13/891,378, dated Sep. 25, 2014.
Office Action for U.S. Appl. No. 13/891,378, mailed May 20, 2014.
Office Action for U.S. Appl. No. 13/558,789, dated Oct. 7, 2014.
PCT International Search Report for Application No. PCT/EP2010/070360, dated Aug. 7, 2012.
PCT International Search Report for Application No. PCT/EP2010/070361 dated Dec. 21, 2010.
Office Action mailed May 19, 2015 for U.S. Appl. No. 13/891,378.

* cited by examiner

IMPLANT FOR STABILIZING SPINOUS PROCESSES

CROSS-REFERENCE TO RELATED APPLICATIONS

This application is a continuation of international application number PCT/EP2013/059722, filed on May 10, 2013, which claims the benefit of U.S. application No. 61/645,716, filed May 11, 2012, the contents of both applications being incorporated herein by reference in their entirety and for all purposes.

FIELD

The present invention relates to an implant for stabilizing spinous processes of adjacent vertebral bodies relative to one another, comprising a first contact element and a second contact element, wherein, to stabilize the spinous processes, the first contact element can be placed laterally on a first side of the spinous processes and the second contact element can be placed laterally on a second side of the spinous processes, which is remote from the first side, and wherein the implant comprises at least one clamping element, coupling to the first contact element, and movable relative to the second contact element, the clamping element extending through the intervertebral space between the spinous processes and the second contact element, as well as at least one fixing element, which is arranged on the second contact element and which can be brought into engagement with the at least one clamping element to clamp the second contact element in the direction of the first contact element along the clamping element.

BACKGROUND

An implant of this type is disclosed in international application PCT/EP2011/069895. It allows the stabilization of the spinous processes of adjacent vertebral bodies, "adjacent" primarily being able to mean "directly adjacent" but, in the present case, not being limited to directly adjacent vertebral bodies. In the present case, "vertebral body" designates both the vertebra overall ("vertebra") and also the vertebral body in the narrower sense ("corpus vertebrae"). Anatomical position and direction details, such as, for example, "lateral", "cranial", "caudal" or the like are, in the present case, to be understood as relating to the intended use of the implant, in which the contact elements abut laterally on the mutually remote sides of the spinous processes and may have a cranial-caudal orientation.

In the known implant, two clamping elements fixed to the first contact element extend through the intervertebral space and the second contact element, which comprises fixing elements and, by means of these, has a latching engagement with the clamping elements. This allows the contact elements to be clamped relative to one another, and by means of their abutment, allows the spinous processes to be stabilized relative to one another. For this purpose, the implant further comprises at least one spacer element positioned in the intermediate space and fixed by means of the contact elements. The spacer element, on the one hand, allows a checking of the spacing of the contact elements from one another and, on the other hand, can be supported on the spinous processes, for example cranially and/or caudally.

The implant proves successful in practice. However, it would be desirable to provide an implant that can be handled more easily.

Further implants for the mutual support of spinous processes are described, for example, in EP 1 885 266 B1, US 2009/0264927 A1 and WO 2011/031924 A2.

An object underlying the present invention is to provide an implant of the above type, which can be handled more easily.

SUMMARY

In an aspect of the invention an implant for stabilizing spinous processes of adjacent vertebral bodies relative to one another comprises a first contact element and a second contact element, wherein, to stabilize the spinous processes, the first contact element can be placed laterally on a first side of the spinous processes and the second contact element can be placed laterally on a second side of the spinous processes, which is remote from the first side. The implant comprises at least one clamping element, coupling to the first contact element, and movable relative to the second contact element, the clamping element extending through the intervertebral space between the spinous processes and the second contact element, as well as at least one fixing element, which is arranged on the second contact element and which can be brought into engagement with the at least one clamping element to clamp the second contact element in the direction of the first contact element along the clamping element. The first contact element is movable relative to the at least one clamping element in the longitudinal direction thereof, and the at least one clamping element comprises at least one support member for support directly or indirectly on the first contact element against a movement in the direction of the second contact element.

BRIEF DESCRIPTION OF THE DRAWINGS

The foregoing summary and the following description may be better understood in conjunction with the drawing figures, of which.

DETAILED DESCRIPTION

Figure 1:
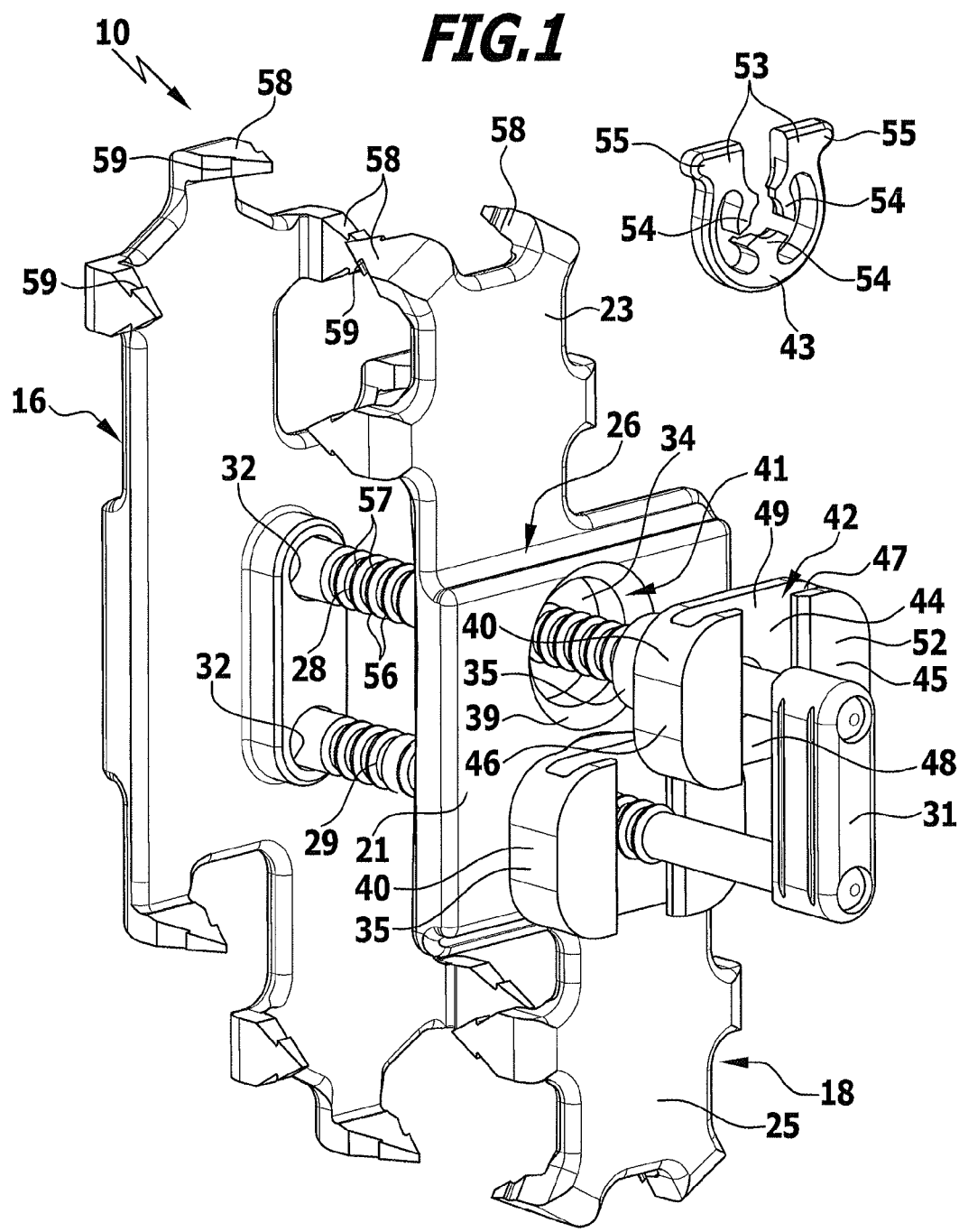
FIG. 1: shows a perspective view of a first preferred embodiment of an implant in accordance with the invention, partly in an exploded view.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an implant for stabilizing spinous processes of adjacent vertebral bodies relative to one another, comprising a first contact element and a second contact element, wherein, to stabilize the spinous processes, the first contact element can be placed laterally on a first side of the spinous processes and the second contact element can be placed laterally on a second side of the spinous processes, which is remote from the first side, and wherein the implant comprises at least one clamping element, coupling to the first contact element, and movable relative to the second contact element, the clamping element extending through the intervertebral space between the spinous processes and the second contact element, as well as at least one fixing element, which is arranged on the second contact element and which can be brought into engagement with the at least one clamping element to clamp the second contact element in the direction of the first contact element along the clamping element. The first contact element is movable relative to the at least one clamping element in the longitudinal direction thereof, and the at least one clamping element comprises at least one support member for support directly or indirectly on the first contact element against a movement in the direction of the second contact element.

Unlike the implant described above, in the implant in accordance with the invention the first contact element is movable relative to the at least one clamping element in its longitudinal direction. The first contact element and the second contact element can thus more easily adopt different spacings relative to one another. This proves to be advantageous for handling, in particular during insertion of the implant and its positioning on the spinous processes, as it allows a variable prepositioning of the implant on the spinous processes with movement of the contact elements toward one another or away from one another, without the second contact element already being fixed relative to the clamping element by means of the at least one fixing element and being clamped in the direction of the first contact element. During the prepositioning, the operator can place the contact elements, even repeatedly, loosely or only lightly on the spinous processes and check them with respect to their final position. To lock the implant, in particular the clamping element extending through the second contact element can be loaded with a pulling force directed away from the second contact element. This provides the possibility of coupling the clamping element to the first contact element, the at least one support member being supported on the first contact element and being blocked from further movement in the direction of the second contact element. The clamping element may be supported directly on the first contact element by means of the support member, in particular on the side of the first contact element remote from the second contact element, an indirect support also being possible. The prepositioned implant can thus be fixed in its position with clamping of the second contact element in the direction of the first contact element by means of the fixing element.

The implant in accordance with the invention can also be positioned and locked on the spinous processes by an only a comparatively small access with slight muscle detachment. This allows the stress for the patient to be minimized.

The at least one clamping element may be pin-like or rod-like in configuration.

It is favorable if the at least one fixing element can be brought into latching and/or clamping engagement with the at least one clamping element and comprises fixing members, which, with an existing engagement, abut the at least one clamping element and allow a movement of the fixing element only in the direction of the first contact element. The fixing element may, for example, be bow-like or in the form of an open ring and have two ends that are elastically resilient relative to one another, which engage around the clamping element. This allows the fixing element to be placed on the clamping element transverse to its longitudinal direction and to be fixed thereon. The fixing members may be tongues or projections on the fixing element, which can engage in peripheral grooves of the clamping element. The peripheral grooves may be formed between peripheral ribs of the clamping element, which have a saw tooth-like form in cross-section, so the fixing element can be displaced on the clamping element in the direction of the first contact element, but a displacement in the opposite direction is prevented.

It may be provided that the second contact element comprises the at least one fixing element. For example, the latter is formed in one piece with the second contact element and integrated therein.

The at least one fixing element is preferably arranged on a side of the second contact element remote from the first contact element. The fixing element may, for example, by a movement in the direction of the first contact element, contact the second contact element and clamp it in the direction of the first contact element.

The at least one fixing element is advantageously preassembled on the at least one clamping element in order to facilitate the handling of the implant. This provides the possibility of introducing the implant in the preassembled state into the body of the patient and correctly positioning it on the spinous processes. The implant can then be locked without the fixing element having to be introduced separately for this into the body and having to be positioned on the clamping element. For example, the fixing element has a latching engagement with the clamping element, said fixing element engaging in a peripheral groove between two peripheral ribs of the clamping element.

The at least one fixing element can preferably be released from the at least one clamping element in order to release the clamping of the second contact element in the direction of the first contact element. As a result, the position of the implant relative to the spinous processes can be changed, for example, in the course of a correction procedure, or the implant can be removed from the body. To release the fixing element, it can, in particular, be disengaged from the clamping element, for example, a latching engagement between the fixing element and the clamping element is released.

In general, it is favorable if an engagement of the at least one fixing element with the at least one clamping element can be released, for example in order to move the fixing element in a direction away from the first contact element along the clamping element or to move the fixing element transverse to the direction of the clamping element.

It may be provided that the at least one fixing element, for example in the case of a bow-like form, can be placed on the clamping element with the ends encompassing the clamping element transverse to the direction of said clamping element. In a corresponding manner, the fixing element can be released from the clamping element transverse to the direction of the clamping element in that the ends are spread apart relative to one another and an engagement with the clamping element can be released.

It is advantageous if the implant has at least one fixing element receptacle, which is arranged on a side of the second contact element remote from the first contact element and in which the at least one fixing element can be positioned, which fixing element receptacle has a first blocking member for the at least one fixing element to block its movement in the direction away from the second contact element and comprises a contact member to absorb a force directed onto the second contact element. The fixing element receptacle may be supported, in particular, on the second contact element in the direction of the first contact element, or it may be formed in one piece with the second contact element. A force can be introduced by the contact member onto the fixing element receptacle and can be transmitted by means of the blocking member onto the fixing element. With an additional action of force on the at least one clamping element, the fixing element can be moved relative to the clamping element in order to clamp the contact elements relative to one another. The fixing element receptacle may be configured as a casing, and it may comprise a, for example, groove-like or slot-like receiving space for the fixing element. In the receiving space, the fixing element may be positioned along the clamping element and/or transverse thereto, in particular without play.

The at least one fixing element receptacle preferably has a second blocking member for the at least one fixing element to block its movement in the direction of the second contact element. This allows the fixing element to be reliably positioned in the fixing element receptacle and thus allows the implant to be reliably fixed on the spinous processes to be stabilized. The second blocking member may, for example, be formed by the second contact element, on which the fixing element can be supported. Furthermore, a force can be introduced by means of the blocking member from the second contact element onto the fixing element, which can be supported on the clamping element.

The at least one fixing element receptacle is preferably dimensioned such that the at least one fixing element is positioned along the clamping element and transversely thereto positively in the fixing element receptacle.

It is advantageous if the at least one fixing element receptacle has a receptacle opening for introducing the at least one fixing element into the fixing element receptacle and/or removing the at least one fixing element from the fixing element receptacle. The fixing element can be introduced through the receptacle opening into the fixing element receptacle or removed therefrom. The fixing element can thus, in particular, be placed on the clamping element and released therefrom. In particular, the fixing element can be introduced transverse to the direction of the clamping element into the fixing element receptacle and/or removed therefrom.

The at least one fixing element is advantageously secured against rotation relative to the at least one fixing element receptacle with respect to a rotation about the at least one clamping element. This proves advantageous, in particular when the fixing element is releasable from the clamping element. The securing against rotation can ensure that the fixing element is accessible with a release tool.

The implant preferably comprises two clamping elements running parallel to one another and arranged at a spacing from one another. This allows the implant to be fixed more reliably on the spinous processes to be stabilized.

The implant preferably comprises two fixing elements, which are each associated with one of the clamping elements. Each of the fixing elements can be brought into engagement with one of the clamping elements in order to contribute to the clamping of the second contact element in the direction of the first contact element. The provision of two fixing elements proves to be advantageous especially when the contact elements tilt relative to one another because of the contour of the spinous processes and thus allows improved adaptation of the implant to the contour of the spinous processes.

In an advantageous embodiment of the implant in accordance with the invention, it is favorable if the fixing elements are arranged in a common fixing element receptacle. The fixing element receptacle can, in particular, comprise a common first blocking member and a common second blocking member for both fixing elements.

In a different type of preferred embodiment of the implant in accordance with the invention, it is favorable if the fixing elements are arranged in different fixing element receptacles. The fixing element receptacles may, in particular, each comprise a first and a second blocking member for the respective fixing element. The fixing element receptacles are, in particular, preferably comprised or formed by articulation elements of an articulation device of the implant, which will be discussed below.

The fixing element receptacles are, in particular, advantageously mutually secured against rotation about the respective clamping element. The relative position of the fixing element receptacles to the clamping elements can be ensured by the securing against rotation. This proves, in particular, to be advantageous if the fixing elements can be introduced into the respective fixing element receptacle and/or removed therefrom, in order to be placed on the respective clamping element or released therefrom.

It is advantageous if the two clamping elements on the side of the second contact element remote from the first contact element are connected to one another by a bridge, which is supported on the clamping elements in the direction away from the second contact element. This proves to be advantageous to clamp the contact elements against one another when fixing the implant on the spinous processes. For example, the bridge may be loaded with a force directed away from the second contact element and, in addition, the contact member, or the contact members, of the fixing element receptacle(s) may be subjected to with a counter-force in the direction toward the second contact element. In a different type of configuration of the implant, the second contact element or the sides of the fixing elements remote from the second contact element can be subjected to the counter-force. This allows the clamping elements to be moved in the direction of the first contact element, until they are directly or indirectly supported thereon and allows the second contact element to be clamped with the fixing elements in the direction of the first contact element.

If only one clamping element is present, it may be provided that on its side remote from the first contact element, a support member is provided, which is supported on the clamping element in the direction away from the second contact element, so a force can correspondingly be introduced onto the clamping element.

It is favorable if the clamping elements are rigidly connected to one another by means of the bridge. This, for example, allows a mutual guidance of the clamping elements during their movement relative to the contact elements.

In a different type of preferred embodiment of the implant in accordance with the invention, it proves to be advantageous if the bridge is movably held on the clamping elements. As a result, the clamping elements may be movable relative to one another. This proves to be advantageous, for example, when the contact elements can tilt relative to one another to be adapted to the contour of the spinous processes.

Alternatively or in addition, it may be provided that the bridge is elastically or plastically deformable in order to also achieve the above-mentioned advantage.

It is favorable if the implant comprises an articulation device, by means of which the first contact element and/or the second contact element is arranged so as to be movable by tilting on the at least one clamping element. The articulation device allows an improved adaptation of the implant to the geometry of the spinous processes. The contact elements can be tilted relative to one another by the articulation device, so they can better be placed on the spinous processes that are generally of in a drop-like shape in the cranial-caudal direction.

The articulation device is advantageously either arranged on the first contact element or on the second contact element, so the at least one clamping element is movable by tilting either relative to the first or relative to the second contact element. Relative to the respective other contact element, the clamping element is advantageously displaceable transverse to its longitudinal direction and preferably guided thereby. This allows the adaptability of the implant to be ensured while at the same time having a structurally simple configuration.

The articulation device preferably comprises at least one articulation element through which the at least one clamping element extends, which articulation element has an articulation face, which cooperates with a corresponding articulation face, which faces away from the second contact element, of the first contact element or with a corresponding articulation face, which faces away from the first contact element, of the second contact element. The respectively cooperating articulation faces of the articulation element and the first or the second contact element preferably have the same curvature and are, in particular, spherical. The articulation element may comprise or form an articulation sleeve, through which the clamping element engages. The articulation element may be supported on the side, which is remote from the other respective contact element, of the first or the second contact element, so an articulated connection is provided between the articulation element and the contact element.

It is advantageous if the at least one clamping element is movable in the longitudinal direction relative to the at least one articulation element. For example, the clamping element may be displaceably guided in the articulation element, which, for this purpose, preferably comprises or forms an articulation sleeve.

In a preferred embodiment of the implant in accordance with the invention, it proves to be advantageous if the at least one articulation element is arranged on the first contact element. The articulation element may be supported on the side, which is remote from the second contact element, on the first contact element. In addition, the clamping element can be supported by the support member mentioned in the introduction on the articulation element against movement in the direction of the second contact element and thereby be supported indirectly on the first contact element. In this embodiment, the clamping element is preferably displaceably guided by the second contact element.

In a different type of preferred embodiment, it proves to be favorable if the at least one articulation element is arranged on the second contact element. The articulation element may be supported on the side of the second contact element remote from the first contact element. The clamping element is preferably displaceably guided in this embodiment by the first contact element.

If more than one clamping element is provided, for example the two clamping elements mentioned above, an articulation element is preferably associated with each clamping element. The articulation elements are preferably arranged on the same one of the contact elements.

It is particularly advantageous if the articulation element arranged on the second contact element comprises or forms the at least one fixing element receptacle for the at least one fixing element. This allows a structurally simple configuration, a compact design and a reliable functioning of the implant. The articulation element is, on the one hand, used for the connection that is movable by tilting of the clamping element to the second contact element. On the other hand, it comprises the above-mentioned fixing element receptacle for the fixing element.

The implant may be produced partly or completely from a metal, such as, for example, titanium or from a plastics material, such as, for example, PEEK. The implant may be completely or partly resorbable.

The contact elements are advantageously planar or substantially planar to allow a compact design of the implant.

It is advantageous if the contact elements in each case comprise a central portion and end portions, which project from the central portion on its mutually opposing sides along a first spatial direction and which are preferably arranged on the central portion offset relative to one another in a second spatial direction transverse to the first spatial direction. This can, in particular, be taken to mean that end portions project cranially and caudally from the central portion and are offset with respect to one another in the dorso-ventral direction, in relation to an intended fixing of the implant on the spinous processes. Furthermore, this can be taken to mean, in particular, that the contact elements are formed in a step-like manner and are formed with two portions, which are offset relative to one another in the cranial-caudal direction and are in each case formed from one of the end portions and a part of the central portion. A configuration of this type of the contact elements proves to be advantageous when a plurality of spinous processes are to be stabilized relative to one another. By means of the end portions, the contact elements can abut on the spinous processes, and the central portion can be arranged in the region of the intervertebral space.

The at least one clamping element may, in particular, extend through the central portion. In a corresponding manner, the at least one fixing element and/or the at least one fixing element receptacle and/or the at least one articulation element may be arranged on the central portion.

It proves to be advantageous if the contact elements comprise or form deformation regions in the transition region from the central portion to the end portions. The contact elements can be deformed at the deformation regions to allow improved adaptation to the contour of the spinous processes.

The deformation regions preferably comprise material weakening regions between the central portion and the end portions. The material weakening may, for example, be based on material removal and/or on the use of a material at the deformation region, which is more easily deformable than the material of the central portion and the end portions. The material weakening regions may comprise bending zones, which, for example, are provided by channel-like or groove-like material recesses at the transition region from the central portion to the end portions.

A deformation region may, for example, also be formed in that the central portion has a greater material thickness than the end portions. The central portion may thereby have a higher rigidity than the end portions, which can be bent for adaptation to the spinous processes relative thereto.

It may be provided that the end portions are pre-bent relative to the central portion in the direction of the respective other contact element or are pre-bent away from the respective other contact element. For example, the cranial end portions may be pre-bent in the direction of the respective other contact element and the caudal end portions may be pre-bent away from the respective other contact element.

The contact elements advantageously comprise engagement members to engage in the spinous processes, which project in the direction of the respective other contact element. A reliable fixing of the contact elements on the spinous processes and therefore a reliable stabilization of the spinous processes relative to one another can be ensured by means of the engagement members. The implant is advantageously free of screws engaging through the spinous processes, so the engagement members allow an engagement in the spinous processes and, at the same time, the danger of a screw pulling out on the spinous processes can be prevented.

The engagement members are preferably arranged on outer edges of the contact elements, for example at free ends of arms on the outer edges of the contact elements, which are bent over in the direction of the respective other contact element.

It is advantageous if the engagement members are arranged on the end portions of the contact elements and if the central portions of the contact elements are free, or substantially free, of engagement members.

The engagement members are preferably at least partly provided at their free ends with barbed shoulders. The shoulders allow the engagement members and, therefore, the contact elements, to be particularly reliably fixed on the spinous processes. The barbed shoulders can give the engagement members an approximately fir tree-like shape, for example.

It proves to be advantageous if the engagement members of the first contact element and of the second contact element are arranged with a gap relative to one another. This allows the two contact elements to be reliably fixed on the spinous processes and the loading on the spinous processes to be kept as small as possible at the same time.

The implant advantageously comprises at least one spacer element, which can be positioned in the intervertebral space and can preferably be fixed by means of the rest of the implant. The spacer element is, for example, engaged with the contact elements and/or the at least one clamping element, for example in a latching and/or clamping manner. The spacer element can be positioned in force—and/or positively-locking manner in the intervertebral space. On the one hand, a support of the vertebral bodies and, in particular of the spinous processes relative to one another can be ensured by the spacer element and, on the other hand, a reliable relative positioning of the contact elements can be made possible. The spacer element may be deformable, it may be elastically deformable, it may be rigid, it may be resorbable, it may be produced from a metal such as titanium, or it may be made of a plastics material such as, for example, PEEK. The spacer element may comprise bone or a bone substitute material, for example hydroxylapatite. Furthermore, the spacer element may be at least partially coated, for example with an osteo-integrative coating, in particular a coating with titanium in powder form.

The at least one spacer element advantageously comprises at least one recess, through which the at least one clamping element extends. For example, this allows a clamping or latching engagement of the spacer element in the clamping element. The recess may have a posterior-side opening, so the rest of the implant can be positioned dorsally while introducing the clamping element into the intervertebral space and into the recess on the spinous processes.

It may also be provided that the articulation element mentioned above of the articulation device can engage in the recess.

It is advantageous if the at least one spacer element comprises or forms a cranial contact face for a spinous process and/or a caudal contact face for a spinous process and/or at least one anterior contact face for at least one of the vertebral bodies, in particular at least one lamina arcus vertebrae. A spinous process situated cranially with respect to the spacer element or a spinous process situated caudally with respect to the spacer element can be supported thereby. A displacement of the spacer element in the direction of the spinal channel can be avoided by the anterior contact face.

In particular, in the last-mentioned embodiment, it may be provided that the at least one spacer element comprises a central portion that can be positioned in the intervertebral space and lateral portions projecting laterally from the central portion on the anterior side. This can, in particular, be taken to mean that lateral portions project from the central portion on mutually remote sides. The lateral portions may be formed as wing-like projections on the central portion. The lateral portions may, in particular, comprise or form anterior contact faces for at least one of the vertebral bodies, in particular for at least one lamina arcus vertebrae. For example, the lateral portions are strip-like and extend in the cranial-caudal direction over the laminae arcus vertebrae of both vertebral bodies.

The at least one spacer element may be wedge-shaped, in particular in the cranial-caudal direction and thereby be adapted to the approximately drop-like shape of the spinous processes.

A different type of preferred embodiment of the implant in accordance with the invention is an implant, which is free of spacer elements and does not comprise a spacer element arranged in the intervertebral space.

The invention furthermore relates to insertion instruments for an implant in accordance with the invention, which has at least one handling device for the implant.

Figure 2:
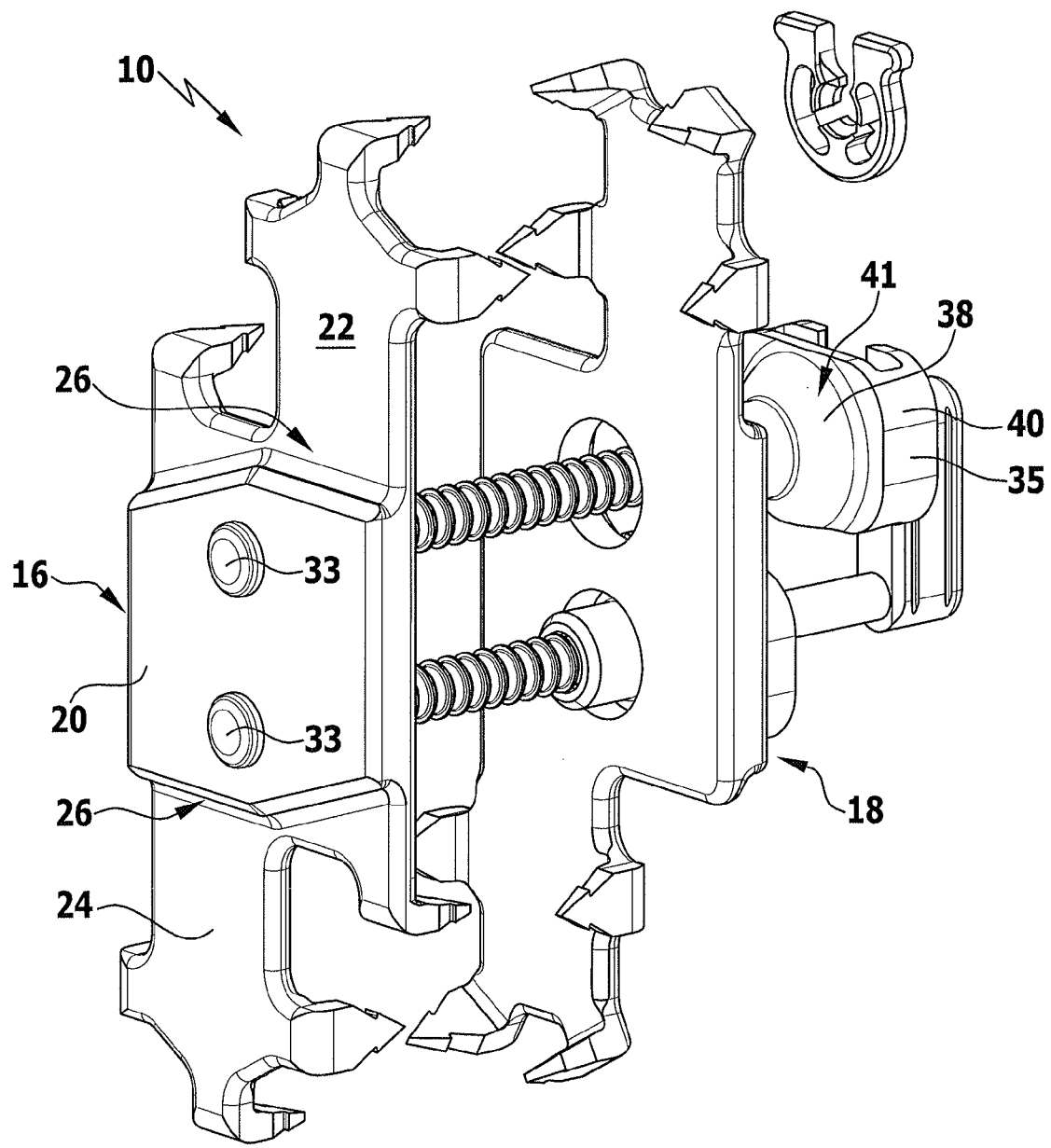
FIG. 2: shows a further perspective view of the implant from FIG. 1.

FIGS. 1 and 2 show, partly in an exploded view, a first preferred embodiment of an implant in accordance with the invention having the reference numeral 10. The implant 10 is used to stabilize spinous processes 12 and 14 of adjacent vertebral bodies 13 or 15 (FIGS. 5 to 8 and 13).

To stabilize the spinous processes 12 and 14, the implant 10 has a first contact element 16 and a second contact element 18. The contact elements 16 and 18 may be placed laterally on mutually remote sides 17 or 19 on the spinous processes 12 and 14 and partly penetrate them, which will be discussed below.

The contact elements 16 and 18 are substantially plate-like and in each case have a central portion 20 or 21, which is right-angular and approximately square in plan view. Cranial end portions 22 or 23, which are approximately right-angular in plan view, project from the central portions 20 and 21 in the cranial direction. In a corresponding manner, caudal end portions 24 or 25 that are approximately right-angular in plan view project from the central portions 20 and 21 in the caudal direction. The position and orientation details such as, for example, "cranial", "caudal" and the like are in the present case to be understood as relating to an intended use of the implant 10, in which the implant 10 is oriented in the cranial-caudal direction to stabilize the spinous processes 12 and 14.

The end portions 22 and 24 as well as 23 and 25 are arranged offset with respect to one another on the central portion 20 or 21 transverse to the longitudinal direction of the contact elements 16 or 18, i.e. in the dorso-ventral direction in the intended use. The contact elements 16 and 18 therefore have an approximately step-like contour in the cranial-caudal direction. This proves to be advantageous when a plurality of spinous processes is to be stabilized relative to one another, cranial end portions 22 of a caudally arranged first contact element 16 being able to be positioned laterally next to caudal end portions 24 of a cranially arranged first contact element 16. In a corresponding manner, cranial end portions 23 of a caudally arranged second contact element 18 can be positioned laterally next to caudal end portions 25 of a cranially arranged second contact element 18.

The dorso-ventral offset between the end portions 22 and 23 as well as 24 and 25 are identical, so the end portions 22 and 23 and the end portions 24 and 25 oppose one another. The end portions 22 and 24 as well as 23 and 25 are the same size and, in the cranial-caudal direction, the longitudinal ratio of the end portions 22 to 25 to the central portions 20 and 21 is approximately 1:1 to about 2:1.

The material thickness of the, in particular, one-piece contact elements 16 and 18 at the central portions 20 or 21 is greater than at the end portions 22, 24 or 23, 25. In transition regions from the central portions 20, 21 to the end portions 22, 24 or 23, 25, deformation regions 26 are thereby formed in each case. At the deformation regions 26, the end portions 22, 24 can be bent relative to the portion 20 and the end portions 23, 25 can be bent relative to the portion 21 in the direction of the respective other contact element 16 or 18, or can be bent away therefrom. This allows an adaptation of the contour of the contact elements 16, 18 to the form of the spinous processes 12 and 14, which is approximately drop-shaped in the cranial-caudal direction.

The contact elements 16 and 18, at their outer edges, have engagement members to engage in the spinous processes in the form of projections 58 facing the respective other contact element 16, 18. The projections 58 are arranged on arms projecting from the contact elements 16 and 18, the ends of which arms are bent over in the direction of the respective other contact element 16, 18. The end portions 22 and 24 in each case have three projections 58 and a central portion 20 has two projections 58. In comparison, the end portions 23 and 25 in each case have four projections, and the central portion 21 of the contact element 18 is free of projections.

Figure 8:
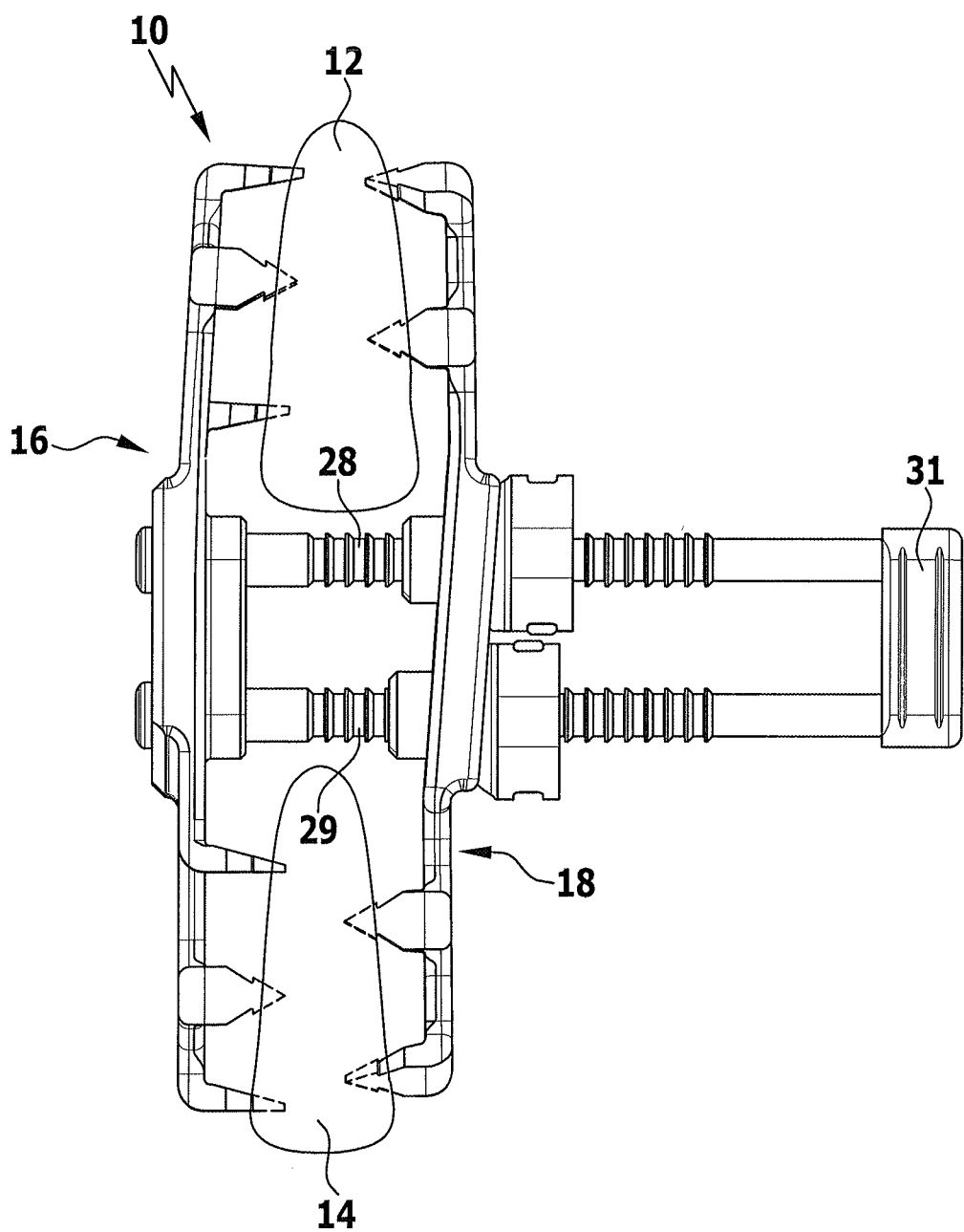
FIG. 8: shows a view corresponding to FIG. 5, in which the contact elements are engaged with the spinous processes and stabilize them relative to one another.

The projections 58 of the contact elements 16 and 18 are arranged staggered with respect to one another, so the projections 58 of the contact elements 16 and 18, when the implant 10 is in use, do not directly oppose one another (FIG. 8).

The projections 58 are furthermore provided at their free ends with barbed shoulders 59, in order to allow improved anchoring of the projections 58 in the spinous processes 12 and 14. Owing to the shoulders 59, the projections 58 have an approximately fir tree-like shape.

The contact elements 16 and 18 may be clamped relative to one another for fixing to the spinous processes 12 and 14 in the medial-lateral direction. For this purpose, the implant 10 comprises two clamping elements 28 and 29, which are arranged parallel to one another, run at a spacing from one another and, in the intended use of the implant 10, extend through the intervertebral space 30 between the spinous processes 12 and 14 and relative to which the contact elements 16, 18 are movable. The clamping elements 28 and 29 are connected to one another by means of a bridge 31 at the end at the side of the second contact element 18 remote from the first contact element 16. The bridge 31, in the present case, is rigid and, for example, pressed, screwed or riveted to the clamping elements 28 and 29. The bridge 31 may also be arranged at a spacing from the ends of the clamping elements 28 and 29 at their end remote from the first contact element 16.

The structure and mode of functioning of the clamping elements 28 and 29 is identical, so that substantially only the clamping element 28 will be discussed below.

The clamping element 28 is displaceable relative to the first contact element 16 in a direction oriented transverse to its plane, which is defined by the clamping element 28. The clamping element 28 is pin-like and extends through a through-hole 32 on the central portion 20, so the contact element 16 forms a sleeve for the clamping element 28, in which the latter is displaceably mounted relative to the contact element 16. Conversely, the contact element 16 can be displaced along the clamping element 28 in the direction of the contact element 18 and away therefrom.

At the end remote from the bridge 31, the clamping element 28 comprises a support member 33 in the form of a head, which can be formed in one piece with the clamping element 28. The head may, for example, also be screwed onto the clamping element 28, pressed or riveted thereto. By means of the support member 33, the clamping element 28 can be coupled to the contact element 16 and secured against a movement in the direction of the contact element 18. In this case, the support member 33 and the contact element 16 act together in the form of mutual stop members directly to support the clamping element 28 on the contact element 16.

The clamping element 28 furthermore extends through the contact element 18, in which a through-hole 34 is formed, the diameter of which is approximately twice as large as that of the clamping element 28. A guide element 35 is inserted in the through-hole 34 from the side of the contact element 18 remote from the contact element 16. The guide element 35 is sleeve-like and has the clamping element 28 extending through it, it being configured for the displaceable mounting thereof. The guide element 35 has a shaft portion 36 and a head portion 37. The shaft portion 36 extends through the contact element 18 and projects therefrom partly in the direction of the contact element 16. The external diameter of the shaft portion 36 is smaller than the diameter of the through-hole 34.

The head portion 37 has an articulation face 38, which faces the contact element 18 and can cooperate with an articulation face 39 of the contact element 18 corresponding thereto. The articulation face 39 is arranged on the contact element 18 on the side remote from the contact element 16. The articulation faces 38 and 39, in the present case, have the same degree of curvature. In particular, the articulation faces 38 and 39 have a spherical curvature.

The guide element 35 can be supported on the contact element 18 in the direction of the contact element 16 by means of the articulation faces 38 and 39. At the same time, the guide element 35, and therefore the clamping element 28 guided therein, is movable by tilting relative to the contact element 18. The support that can be moved by tilting of the contact element 18 by the guide element 35 on the clamping element 28 allows an improved adaptation of the implant 10 to the contour of the spinous processes 12 and 14 during its intended use.

The guide element 35, because of the articulated support on the contact element 18, is also called an articulation element 40 and is a component of an articulation device 41 of the implant 10. The articulation device 41 comprises the articulation element 40 as well as the articulation element 40 associated with the clamping element 29 and the contact element 18.

On the side remote from the contact element 18, the guide element 35 has a fixing element receptacle 42 for a fixing element 43, which is provided to block the movement of the guide element 35, and therefore of the contact element 18, relative to the clamping element 28 and therefore to lock the implant 10 in the manner described below.

The fixing element receptacle 42 is configured as a casing and on the head portion 37 has a receiving space 44 for the fixing element 43. The receiving space 44 is shaft-like in the present case, approximately in the form of a T-groove. On the side remote from the contact element 18, the receiving space 44 is limited by a wall 45, which is connected by lateral walls 46, 47 of the receiving space 44 to the rest of the head portion 37. Formed in the wall 45 is a through-hole 48, which is slot-like in the present case, and, to a certain extent, forms the longitudinal line of the T of the cross-sectionally T-like groove. The clamping element 28 extends through the receiving space 44 and the through-hole 48 and leaves the guide element 35 on the side remote from the contact element 18.

Figure 5:
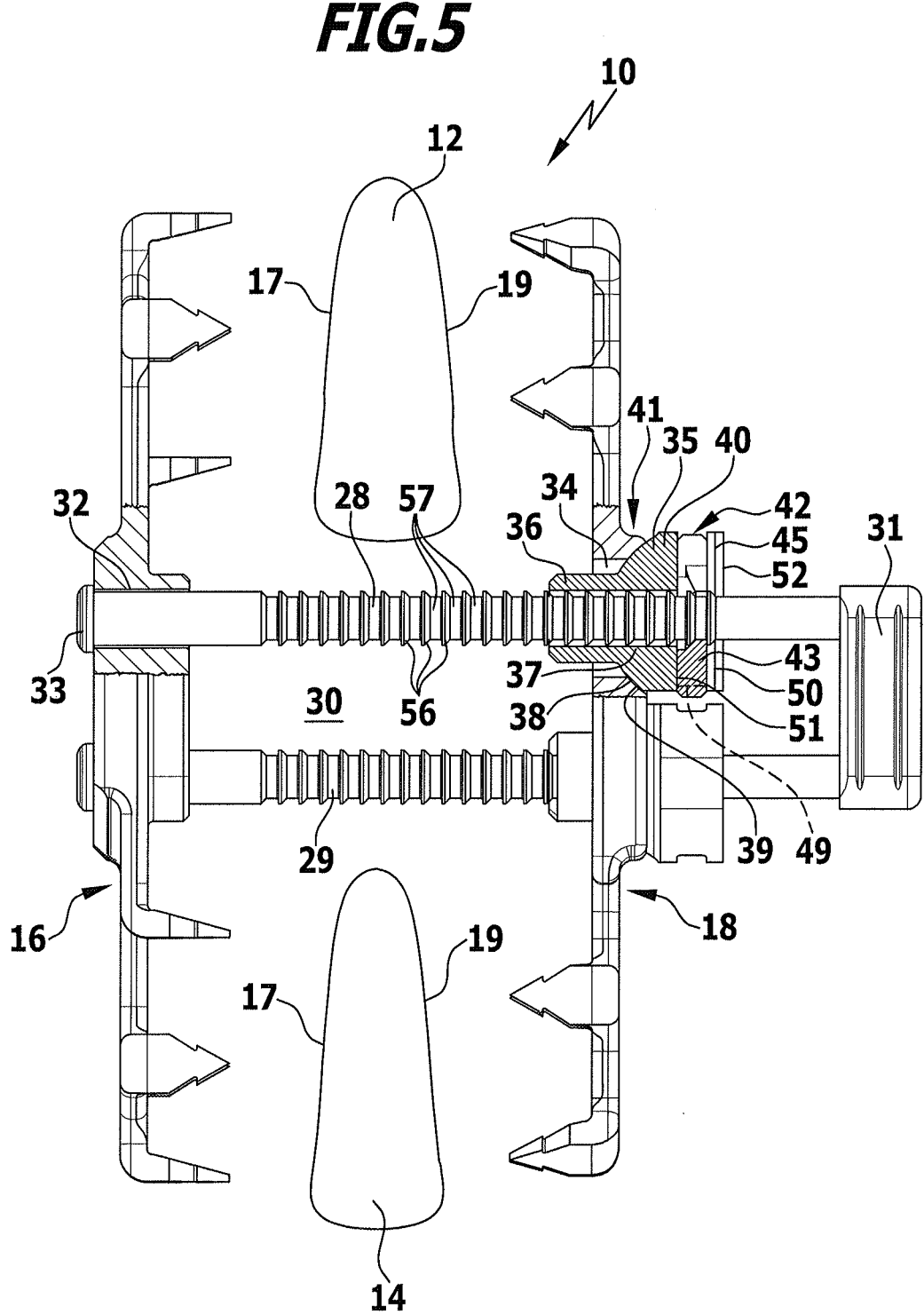
FIG. 5: shows a side view of the implant from FIG. 1, partly in section, in which two contact elements of the implant adopt a first relative position with respect to one another, as well as schematically shown spinous processes.

On the cranial side and on the caudal side, the fixing element receptacle 42 comprises mutually opposing openings 49. The fixing element 43 can be introduced into the receiving space 44 through the openings 49. If the guide element 35 has already been pushed onto the clamping element 28, the fixing element 43 can be introduced through one of the openings 49 into the receiving space 44 and placed on the clamping element 28. In the orientation of the fixing element 43, which is shown in FIGS. 1, 2 and 5, with open ends 53 directed cranially, this takes place caudally or by introduction cranially and subsequent rotation of the guide element 35 relative to the clamping element 28. In the reverse manner, the fixing element 43 can be detached from the clamping element 28 and removed from the receiving space 44 by way of an opening 49. The fixing element 43 is in each case moved into the receiving space 44 or moved out therefrom transverse to the direction of the clamping element 28.

The fixing element receptacle 42 is dimensioned such that the fixing element 43 along the clamping element 28 is positively positioned in the receiving space 44. An inside of the wall 45 facing the receiving space 44 in this case forms a first blocking member 50 divided into two to prevent a movement of the fixing element 43 in the direction away from the second contact element 18. The wall of the receiving space 44 opposing the first blocking member 50 forms a second blocking member 51 to prevent a movement of the fixing element 43 in the direction of the second contact element 18. The fixing element 43 can be supported on the blocking members 50 and 51.

The side of the wall 45 remote from the first blocking member 50 forms a contact member 52 divided into two, on which a force directed onto the contact element 18 is to be applied, in order to move said contact member in the direction of the contact element 16.

The fixing element 43 is configured as an open ring, which can be placed on the clamping element 28 by introduction into the receiving space 44. For this purpose, and to release the fixing element 43 from the clamping element 28, the fixing element 43 can be elastically deformed, the open ends 53 thereof being spread apart relative to one another. Radially on the inside, the fixing element 43 has three protruding fixing members 54. The fixing members 54, in relation to the arrangement of the fixing element 43 on the clamping element 28, are spaced apart from one another in the peripheral direction of the clamping element 28 and in each case cover a limited angular range, for example from about 30° to about 60°. Projections 55 having a cam-like form project radially outwardly from the open ends 53.

The clamping element 28 has a large number of projections equidistantly spaced apart from one another in the longitudinal direction in the form of peripheral ribs 56. The peripheral ribs 56 extend approximately over half the length of the clamping element 28 in the central portion thereof. The peripheral ribs 56 have a saw tooth-like cross-section with an oblique face directed towards the contact element 18 and a blocking face, which is directed to the contact element 16 and is oriented transverse to the longitudinal direction of the clamping element 28.

Recesses in the form of peripheral grooves 57 which, in the direction of the contact element 18, are limited by the above-mentioned blocking faces and are limited in the direction of the contact element 16 by the above-mentioned oblique faces, are formed between peripheral ribs 56 on the clamping element 28.

The fixing element 43 may be brought into latching engagement with the clamping element 28. For this purpose, the fixing element 43 is introduced into the receiving space 44 and placed on the clamping element 28. The projections 55 can latch with the lateral walls 46 and 47 so that the fixing element 43 is secured against release in the fixing element receptacle 42. Transverse to the longitudinal direction of the clamping element 28 and transverse to the introduction direction into the receiving space 44, the fixing element 43 is also secured against movement; in particular, the fixing element 43 is secured against rotation in the fixing element receptacle 42.

However, the fixing element 43 in the fixing element receptacle 42 has enough play that the open ends 53 can be spread apart relative to one another and therefore the engagement with the clamping element 28 can be released.

When there is an existing engagement of the fixing element 43 and the clamping element 28, the fixing members 54 engage in the peripheral grooves 57. If the fixing element 43 is displaced in the direction of the contact element 16 along the clamping element 28, it can slide across the above-mentioned oblique faces and be transferred into an adjacent peripheral groove. In contrast to this, a movement of the fixing element 43 away from the contact element 16 is blocked by the above-mentioned blocking faces of the peripheral grooves 56.

In FIGS. 1 and 2, only one fixing element 43 of the guide element 35 on the cranial side is shown. A fixing element 43, not shown in the drawings, is also associated with the guide element 35 on the caudal side. This fixing element 43 can, in particular, be introduced cranially into the receiving space 44 of the guide element 35 on the caudal side. Alternatively, a caudal introduction with a subsequent rotation of the guide element 35 relative to the clamping element 29 is possible.

The two guide elements 35 can mutually secure each other against a respective rotation about the clamping element 28 or 29.

If the engagement of one of the fixing elements 43 to the respective clamping element 28, 29 is released, the fixing element 43 and the guide element 35 receiving it can be moved along the clamping element 28, 29 with the release of the securing against rotation. The guide element 35 can then be rotated about the clamping element 28, 29 in order to remove the fixing element 43 from the receiving space.

If the clamping elements 28, 29 are spaced apart from one another further than in the implant 10, it may also be provided that an introduction of the fixing element 43 into the receiving space 44 of a guide element 35 can take place from the side of the respective other guide element 35 and/or a removal of the fixing element 43 can take place from the receiving space 44 in the direction of the respective other guide element 35.

A set of insertion instruments for the implant 10 is also the subject of the present invention. A first handling device 60 or a second handling device 61 of a preferred embodiment of a set of instruments in accordance with the invention is shown respectively in FIGS. 3A and 4A.

The first handling device 60 may, in particular, have a first tool part 62 and a second tool part 63, the distal ends 64 or 65 of which are movable relative to one another, and can, in particular, be spread apart relative to one another. This, for example, takes place by spreading the tool parts 62 and 63 of the tong-like handling device 60 apart relative to one another.

A first receptacle 66, which is slot-like in the present case and is used to receive the first contact element 16, is formed at the distal end 64. In a corresponding manner, a second receptacle 67, which in the present case is also slot-like and is used to receive the second contact element 18, is arranged on the distal end 65. The contact elements 16 and 18 can be releasably fixed, for example, in a clamping or latching manner, in the receptacles 64 or 67. Active locks, for example by means of a bayonet-type connection, by screwing or by means of pins, are also conceivable.

Arranged laterally next to the second receptacle 67 at the distal end 65 is a third receptacle 68, in which the head portions 37 of both guide elements 35 can be fixed, for example by latching and/or clamping.

An existing engagement of the contact element 18 with the second receptacle 67 can be released in order to release the second tool part 63 from the second contact element 18, which overall facilitates the release of the handling device 60 from the implant 10. For this purpose, the handling device 60 may comprise a release element 69, which, in the present case, is configured as a lever. By actuating the release element 69, the latter is moved in the direction of the second tool part 63 and the second receptacle 67 is thereby expanded.

The tool parts 62 and 63 may be biased towards one another with respect to their closed position in which they are not spread apart. For this purpose, the handling device 60 may have a separate spring element. The biasing may also, as in the present case, arise because of the elasticity of the tool parts 62 and 63, which are connected to one another close to their proximal ends opposing the ends 64 and 65. The handling device 60, for spreading apart, may comprise actuating elements 70 and 71 on the tool parts 62 or 63.

The second handling device 61 may comprise a first tool part 72 and a second tool part 73, the distal ends 74 or 75 of which are movable relative to one another and can, in particular, be spread apart. For example, the tool parts 72 and 73 are pivotably connected to one another relative to one another by means of an articulation 76. The distal ends 74 and 75 may in each case be fork-like and comprise two, for example, tongue-like projections 77. A recess 78, which, for example, is configured as a slot, may be arranged between the projections 77.

Figure 4:
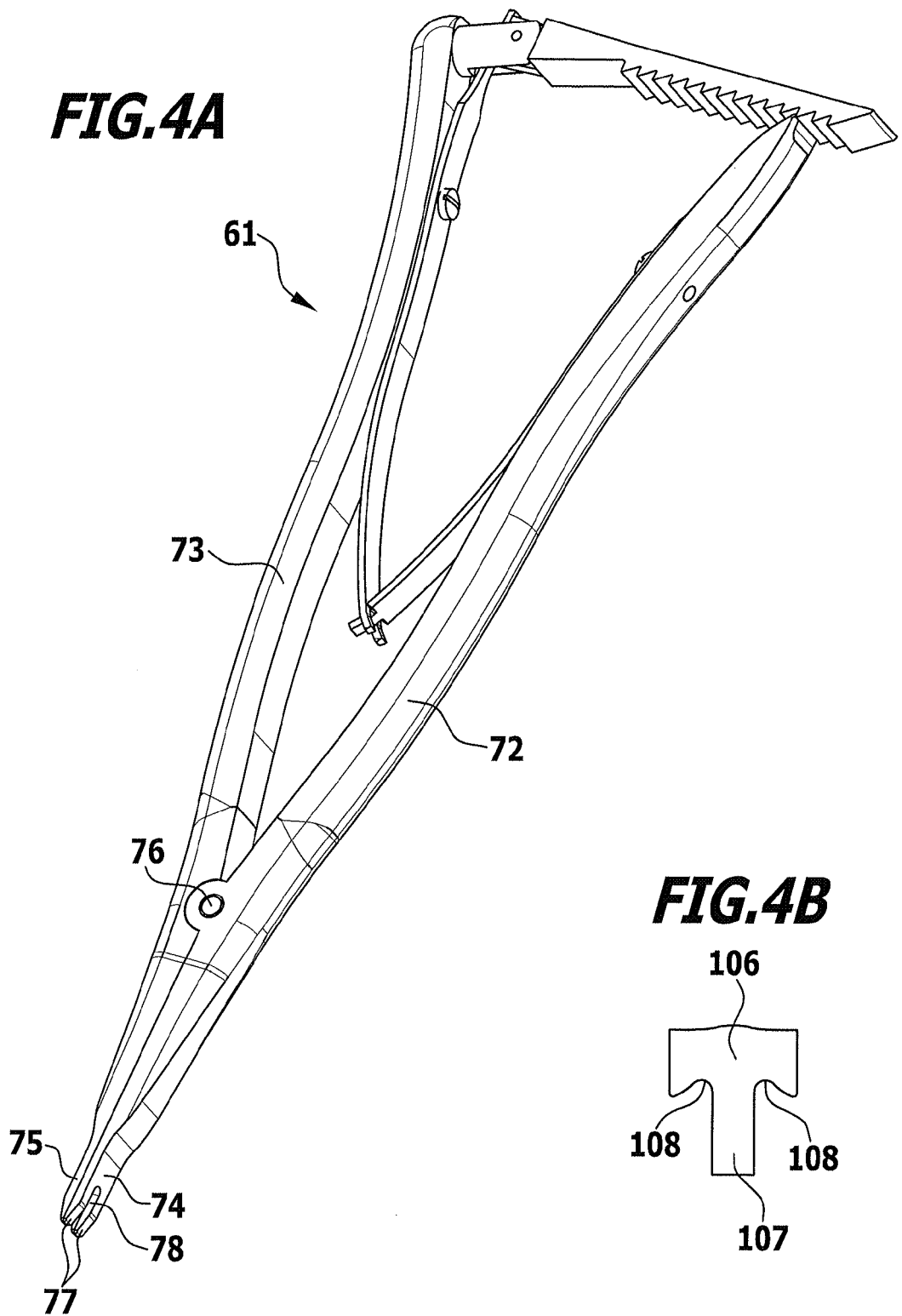
FIG. 4A: shows a further handling device for the implant from FIG. 1.
FIG. 4B: shows a schematic view of a distal end of a further handling device for the implant from FIG. 1 or 10.

The projections 77 of the two tool parts 72 and 73 can abut one another in their closed state and be made congruent, the recesses 78 also being made congruent with one another in this case (FIG. 4A). In a spread-apart state, not shown in the drawings, the projections 77 of both tool parts 72 and 73 can be spaced apart relative to one another.

Figure 6:
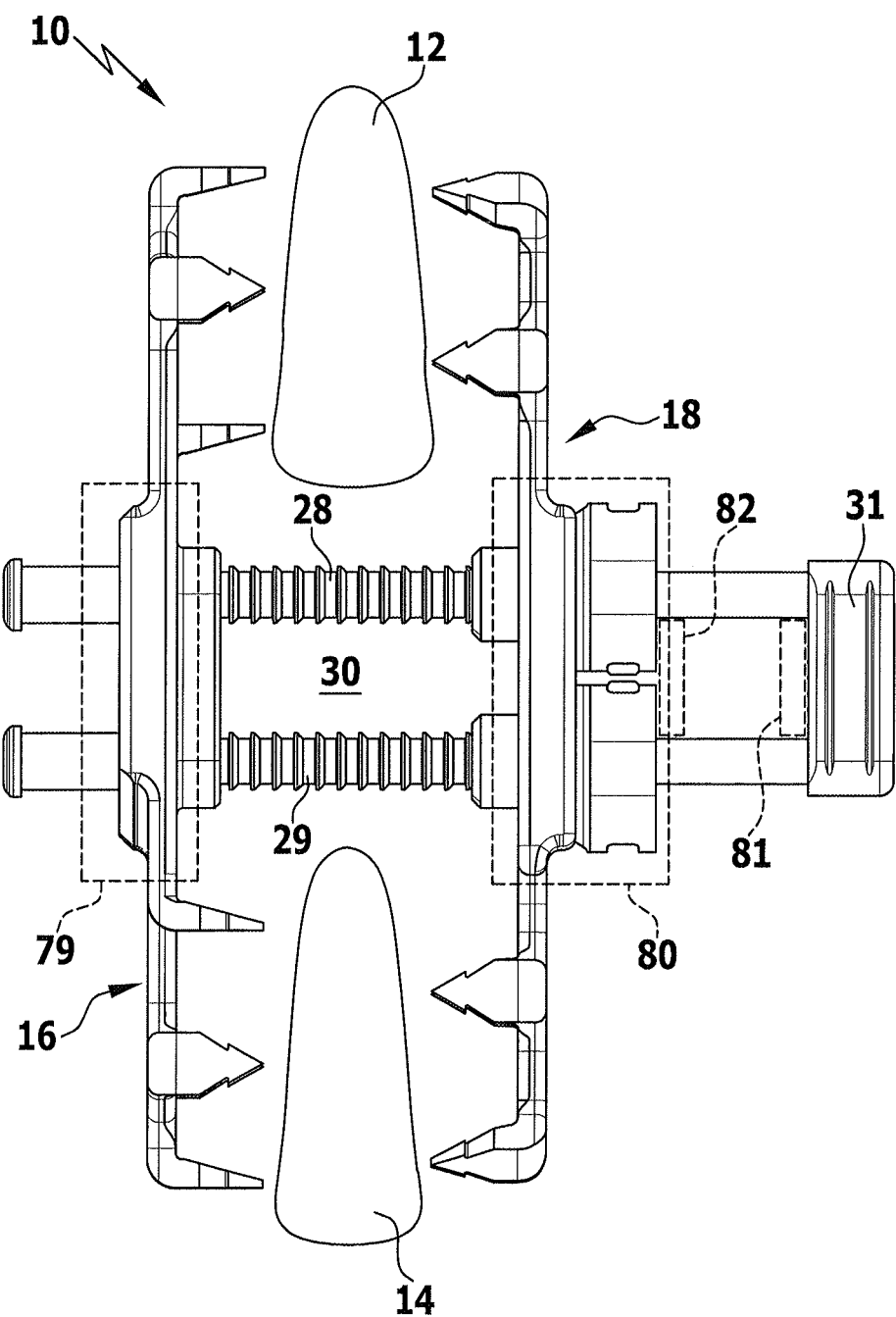
FIG. 6: shows a view corresponding to FIG. 5, in which the contact elements adopt a second relative position with respect to one another.
Figure 7:
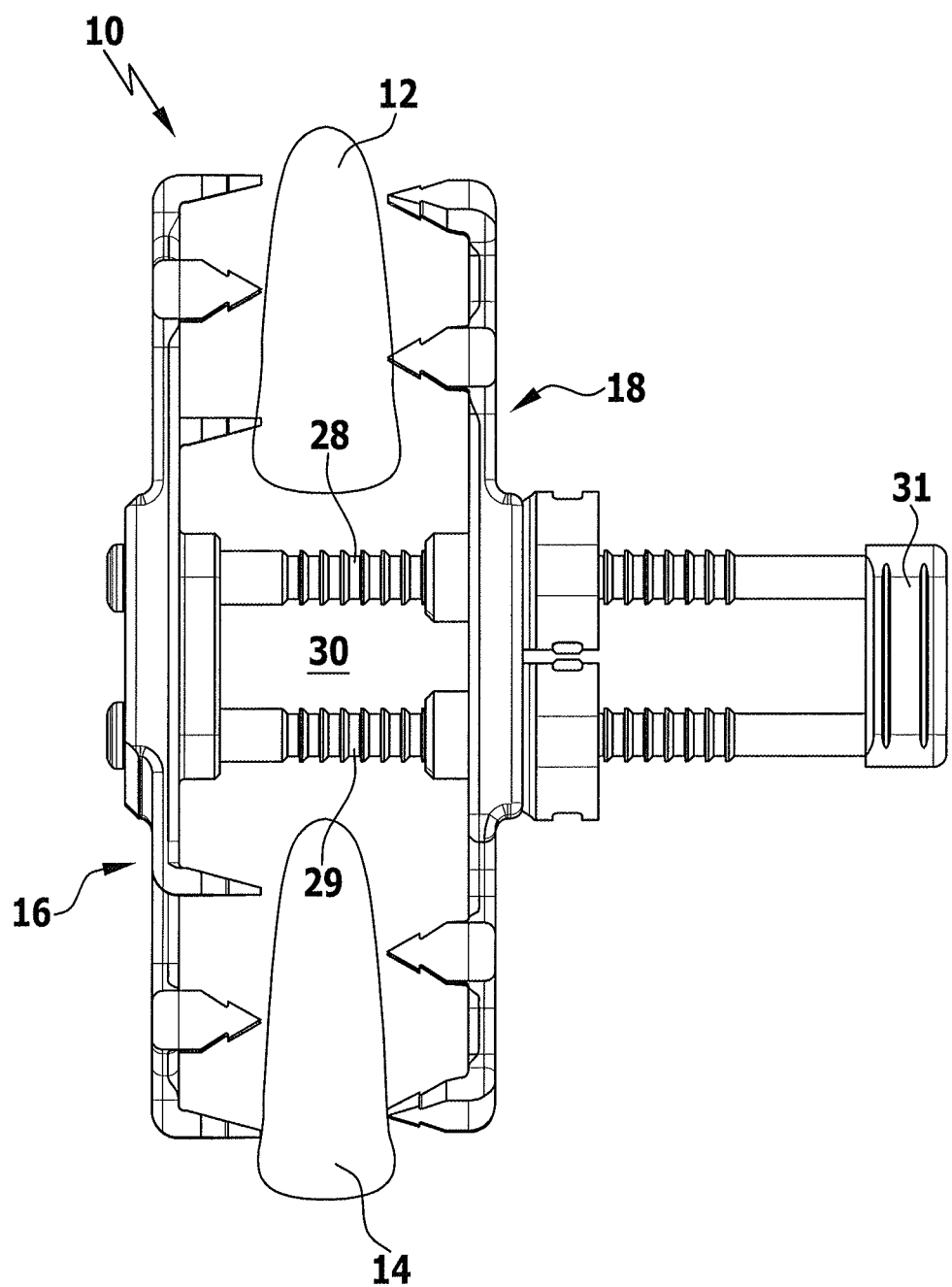
FIG. 7: shows a view corresponding to FIG. 5, in which the contact elements adopt a third relative position with respect to one another.

With reference, in particular, to FIGS. 5 to 8, the functioning and the intended use of the implant 10 using the handling devices 60 and 61 is discussed below. For reasons of clarity only the distal ends 64 and 65 of the tool parts 62 or 63 are shown in FIG. 6 by dashed contours 79 or 80. The distal ends 74 and 75 of the tool parts 72 or 73 are indicated by dashed contours 81 or 82.

In an introduction state, the fixing elements 43 have a latching engagement, preferably preassembled, with the clamping elements 28 and 29, in which they can in particular engage in the peripheral groove 57 closest to the bridge 31 (FIG. 5). The contact element 16 is held in the first receptacle 66, the contact element 18 is held in the second receptacle 67 and the guide elements 35 are held in the third receptacle 68 (cf. FIG. 6). The operator can transfer the contact elements 16 and 18 by means of the handling device 60 into a spread-apart position relative to one another and orient them relative to the spinous processes 12 and 14 to be stabilized. In this case, the operator can orient the contact element 16 in the direction of the lateral side 17 and the contact element 18 in the direction of the lateral side 19. Furthermore, the clamping elements 28 and 29 can extend through the intervertebral space 30.

With approach of the distal ends 64 and 65, the contact elements 16 and 18 can be moved toward one another. In this case, the contact element 16 is displaced relative to the clamping elements 28 and 29 and guided by them, in the direction of the contact element 18 (FIG. 6). The guide elements 35, in contrast, retain their position relative to the contact element 18, as they are held in the third receptacle 68. The free displaceability of the contact element 16 relative to the clamping elements 28 and 29 proves to be particularly advantageous for the handling of the implant 10. The operator is provided with the possibility of positioning the implant 10 only loosely on the spinous processes 12 and 14 or with a slight engagement of the projections 58 therein. In this case, the end portions 22 and 24 can be arranged on the side 17 of the spinous processes 12 or 14 and the end portions 23 and 25 can be arranged on the side 19. Furthermore, the central portions 20 and 21 can be positioned in the region of the intervertebral space 30. Owing to the free displaceability of the contact element 16 on the clamping elements 28 and 29, the spacing of the contact elements 16 and 18 from one another can be repeatedly changed using the handling device 60 and the position of the implant 10 can be corrected until it is correctly positioned relative to the spinous processes 12 and 14.

If the implant 10 adopts the desired position, it can be locked with the aid of the second handling device 61. The distal ends 74 and 75 of the handling device 61 can be introduced laterally past the distal end 65 of the handling device 60 into the intermediate space between the bridge 31 and the guide elements 35, which they can contact, in each case. The implant 10 can be held in the desired position by means of the handling device 60.

When the handling device 61 is actuated, the distal ends 74 and 75 can be spread apart relative to one another. For example, by means of the distal end 74, the bridge 31 can be subjected to a force directed away from the second contact element 18. By means of a distal end 75, a counter-force can be applied to the contact members 52 of the guide elements 35. This results in the clamping elements 28 and 29 being displaced relative to the contact elements 16 and 18 by the force acting on the bridge 31. At the same time, the guide elements 35 and the fixing elements 43 held thereby are displaced relative to the clamping elements 28 and 29, it being possible for the fixing elements 43 to slide along the peripheral ribs 56 and be moved in the direction of the contact element 16.

The loose abutment of the contact elements 16 and 18 on the spinous processes 12 and 14 can be maintained here. It is, of course, also conceivable that the projections 58 can already engage more or less deeply into the spinous processes 12 and 14.

The displacement of the clamping elements 28 and 29 using the handling device 61 can firstly take place until the support members 33 strike against the contact element 16 and couple thereto (FIG. 7), so that the implant 10 is locked by means of the fixing elements 43 and the contact element 18 is clamped in the direction of the contact element 16. A clamping force acting on the contact element 18 can be diverted to the fixing elements 43 by means of the blocking element 51.

With a further force-loading of the bridge 31 and the fixing elements 35, the projections 58 can penetrate, or penetrate more deeply, into the spinous processes 12 and 14 (FIG. 8), the locking of the implant 10 being retained. In particular, penetration into the spinous processes 12 and 14 is possible so deeply that the end portions 22 to 25 contact the spinous processes 12 and 14, preferably in a planar manner or substantially planar (not shown in the drawings). The end portions 22 to 25 therefore form lugs, which can be brought into contact with the spinous processes 12 and 14.

It proves to be advantageous in the implant 10 that it has a high degree of adaptability to the contour of the spinous processes 12 and 14. The contact element 18 can tilt relative to the clamping elements 28 and 29 by means of the articulation device 41. Additionally, the end portions 20 and 24 can be bent relative to the central portion 20 and the end portions 23 and 25 can be bent relative to the central portion 21 in order to allow as good an adaptation as possible to the contour of the spinous processes 12 and 14 (FIG. 8). In the locked state, the implant 10 can be reliably fixed to the spinous processes 12 and 14 to stabilize them relative to one another.

After the fixing, the ends of the clamping elements 28 and 29 projecting beyond the guide elements 35 can be severed by means of a tool, not shown, and removed.

The implant 10, in particular, allows a correction procedure by means of the releasable holding of the fixing elements 43 in the fixing element receptacles 42. By means of a tool, not shown in the drawings, the open ends 53 can be spaced apart relative to one another for correction and the engagement of the fixing element 43 with the clamping element 28, 29 can be released. It proves to be advantageous here if the free ends 53 are directed away from the guide element 35 receiving the other fixing element 43, in each case, and can therefore be more easily reached cranially or caudally (FIGS. 1, 2, 5). After release of the engagement, as mentioned, the guide element 35 can be moved along the clamping element 28, 29. This allows the contact elements 16 and 18 to be spread apart relative to one another, for example to release the implant 10 from the spinous processes 12 and 14. It is, in particular, furthermore possible to rotate the fixing element 35 relative to the clamping element 28, 29 and thereby remove the fixing element 43 from the receiving space 44. However, this is not absolutely necessary in the course of the correction procedure.

Figure 9:
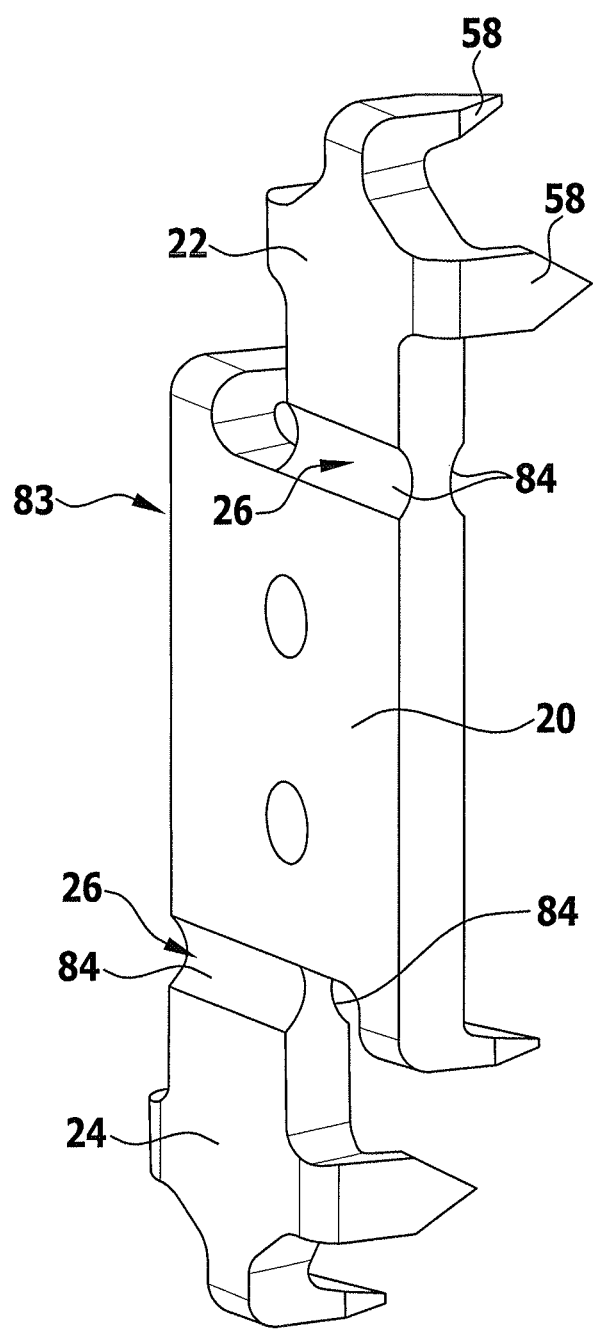
FIG. 9: shows a contact element of an implant in accordance with the invention in a perspective view.

FIG. 9 shows, in a perspective view, a contact element 83, which can be used in the implant 10 instead of the contact element 16. In a corresponding manner, instead of the contact element 18, a contact element, not shown in the drawings, may be used, which also has the properties of the contact element 83.

The contact element 83 differs from the contact element 10 substantially in that it has a uniform material thickness on the central portion 20 and on the end portions 22 and 24. The deformation region 26 is formed in the contact element 83 in that provided on the sides of the end portions 22 and 24 facing the central portion 20 are regions of material removal in the form of grooves 84 on both sides. The grooves 84 form bending zones, on which the end portions 22 and 24 can be bent relative to the central portion 20. The grooves 84 can also be arranged only on the side facing the respective other contact element or on the side remote from the respective other contact element. Differing from the view in accordance with FIG. 9, shoulders 59 from the projections 58 of the contact element 83 may also be present.

Figure 10:
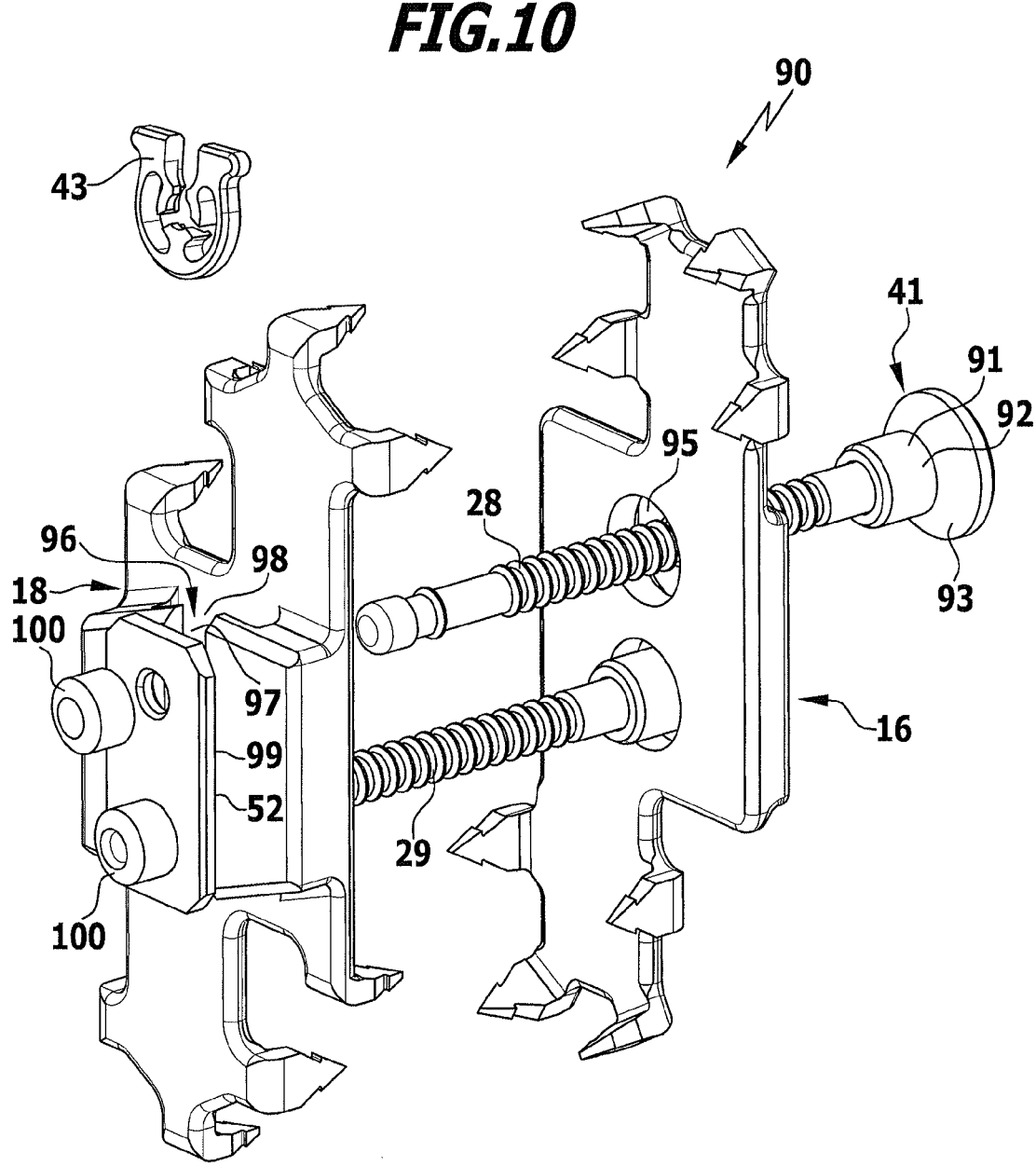
FIG. 10: shows a perspective view of a second preferred embodiment of an implant in accordance with the invention, partly in an exploded view.
Figure 11:
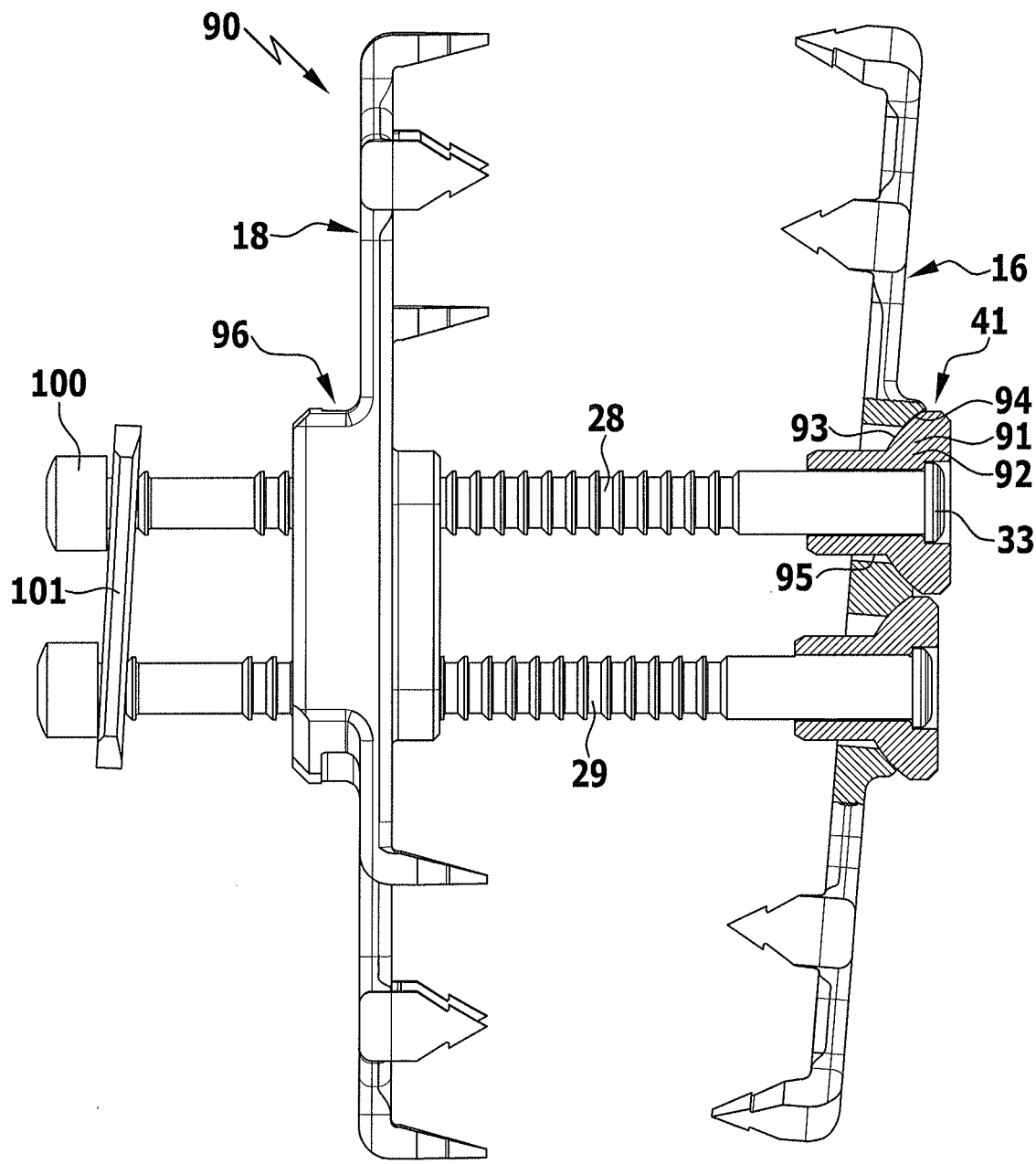
FIG. 11: shows the implant from FIG. 10 in a side view, partly in section.

FIGS. 10 and 11 show a second preferred embodiment of an implant having the reference numeral 90 overall. The same reference numerals are used for features and components of the implants 10 and 90 which are the same and have the same effect, and the advantages that can be achieved with the implant 10 can also be achieved with the implant 90. Only the most important differences between the implants 10 and 90 are discussed.

In the implant 90, instead of the guide elements 35, guide elements 91 are provided, which form articulation elements 92 of the articulation device 41. The articulation elements 92 are arranged on the contact element 16 and have articulation faces 93, which face the contact element 16 and can cooperate with articulation faces 94, which are arranged on the contact element 16 on the side remote from the contact element 18. The articulation elements 92 extend through through-holes 95 in the contact element 16 and are movable by tilting relative thereto.

The clamping element 28 (the same applies to the clamping element 29) extends through the guide element 91 and can be supported by means of the support member 33 on the latter against movement in the direction of the contact element 18. This allows an indirect support and a coupling of the clamping element 28 on or with the contact element 16 against movement in the direction of the contact element 18. The clamping element 28 is displaceably guided in the guide element 91.

In the implant 90, a fixing element receptacle 96 is arranged on the side of the contact element 18 remote from the contact element 16 and configured in one piece therewith, both fixing elements 43 being able to be releasably positioned in said fixing element receptacle to latch with the clamping elements 28 and 29. The fixing element receptacle 96, for this purpose, comprises a receiving space 97, in which the fixing elements can be introduced transverse to the longitudinal axis of the clamping element 28 and can be removed therefrom, specifically through openings 98 on the cranial and caudal side. A wall 99 at a spacing from the contact element 18 corresponds to the wall 45 and forms the first blocking member 50 and the contact member 52. The second blocking member 51 is formed by the central portion 21 of the contact element 18.

The clamping elements 28 and 29 are displaceably guided by the second contact element 18, and they extend through the wall 99. At their ends opposing the support members 33, they comprise the support members 100, in the present case in the form of heads, which are, for example, pressed or screwed onto the clamping elements 28 and 29 or can be welded thereto. A bridge 101 connects the clamping elements 28 and 29 to one another, the bridge 101 being movable by tilting relative thereto and being able to be supported on the support members 100 against movement away from the contact element 18. The bridge 101 could also be supported on the clamping elements 28 and 29 that have been bent over.

Figure 3:
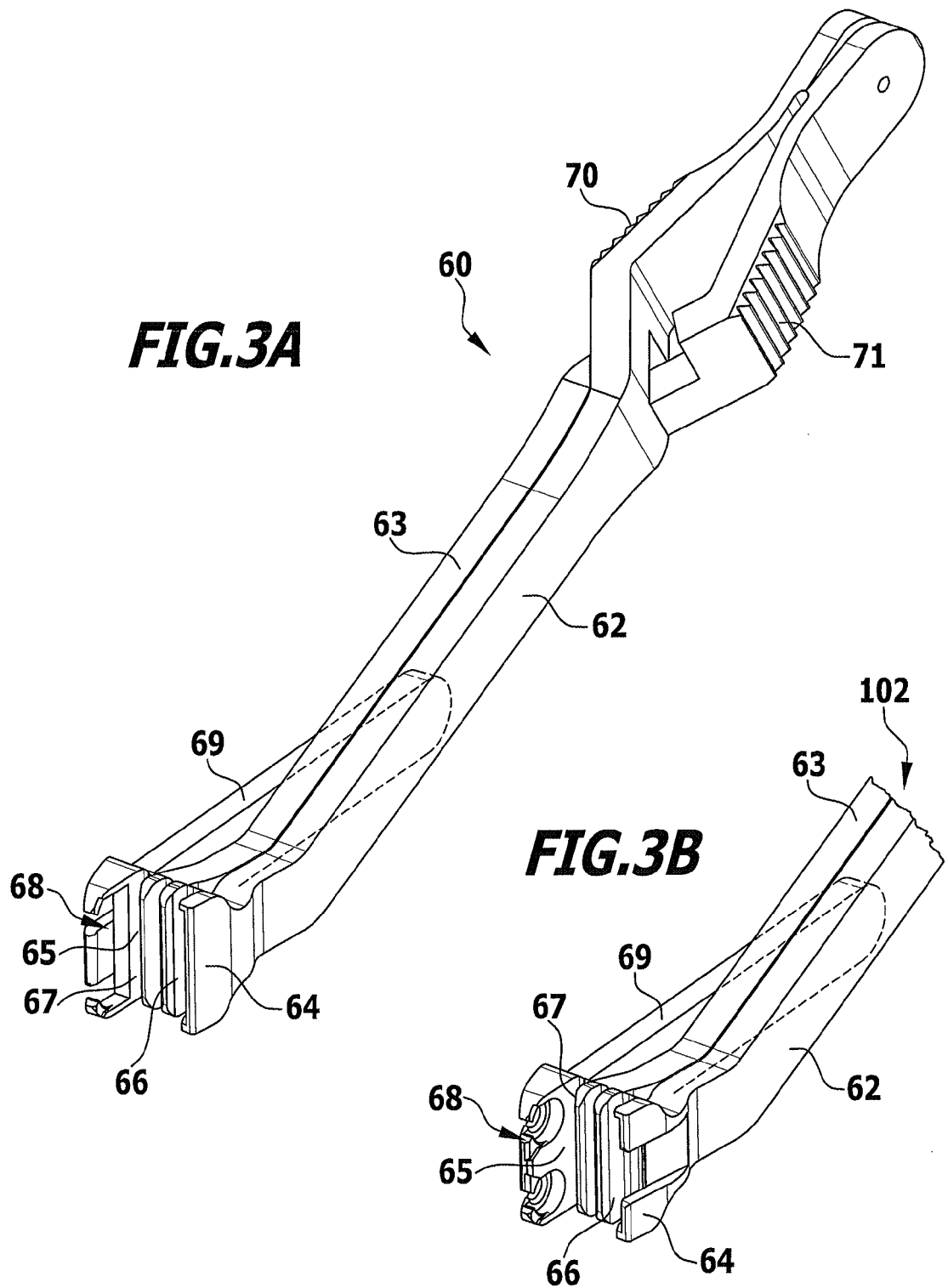
FIG. 3A: shows a handling device for the implant from FIG. 1.
FIG. 3B: shows a view of part of a handling device for the implant from FIG. 10.

A preferred embodiment of a set of instruments in accordance with the invention may comprise the handling device 61 and a handling device 102 partly shown in FIG. 3B, which is configured similarly to the handling device 60 and for the features of which the same reference numerals are used.

During the use of the handling device 102, the first contact element 16 can be introduced into the second receptacle 67 and the head portions of the guide elements 91 can be brought into engagement with the third receptacle 68. The second contact element 18 can be brought into engagement with the first receptacle 66.

The implant 90 is inserted in the manner described above using the example of the implant 10. To position the contact elements 16 and 18 on the spinous processes 12 and 14, the contact element 16 is displaced relative to the clamping elements 28 and 29 in the direction of the contact element 18. The guide elements 91, owing to the arrangement in the third receptacle 68, retain their position on the contact element 16, and the clamping elements 28 and 29 are displaced relative to the guide elements 91.

To lock the implant, the distal ends 74 and 75 of the handling device 61 can be introduced into the intermediate space between the bridge 101 and the contact member 52, in order to subject the bridge 101 to a force directed away from the contact element 18 and to subject the contact member 52 to a counter-force. This can take place until the support members 33 strike against the guide elements 91, are thereby indirectly supported on the contact element 16 and are coupled thereto. The contact elements 16 and 18 are clamped relative to one another with a further application of force by the handling device 61.

A good adaptation to the contour of the spinous processes 12 and 14 can also take place in the implant 90 because of the articulation device 41. Action can also, in particular, be taken on the articulated connection of the clamping elements 28 and 29 by the contact element 16, in that the handling device 61 is positioned on the clamping elements 28 and 29 in such a way that they engage in the recess 78. This provides the possibility of applying a locking force to each of the clamping elements 28 and 29 and transferring the guide elements 91 coupling to them in each case into a tilting position relative to the contact element 16, which allows as good an adaptation as possible of the contour of the implant 90 to the contour of the spinous processes 12 and 14.

Figure 12:
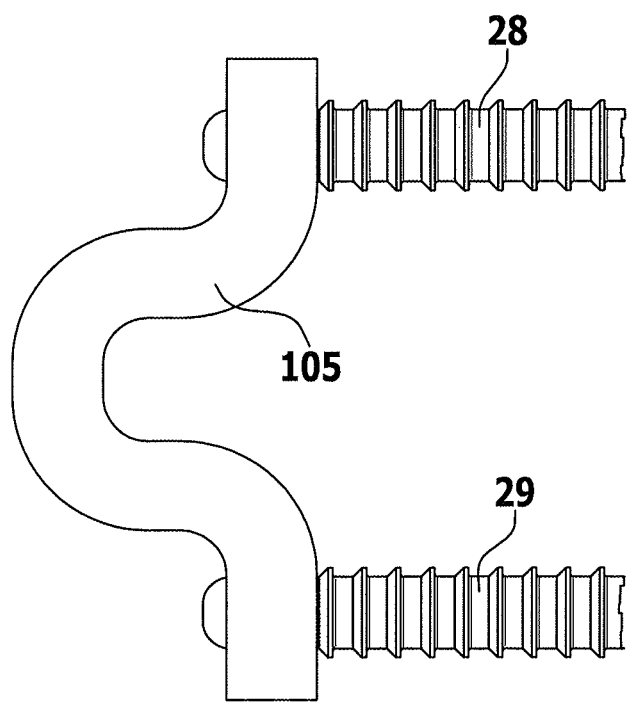
FIG. 12: shows a bridge for connecting two clamping elements of the implant from FIG. 10 to one another.

Instead of the bridge 101 and the support members 100, a bridge 105 shown in FIG. 12 can also be used in the implant 90. The bridge 105 is deformable and, in particular, elastically deformable. The possibility is also thus provided of separately applying locking forces to the clamping elements 28 and 29, and therefore to the respective guide elements 91 coupling thereto, with deformation of the bridge 105.

In the implant 90, the projections 58 of the contact elements 16 and 18 are arranged on the end portions and on the central portions in the reverse manner to in the implant 10.

The fixing elements 43 in the implant 90 can also have a rectangular form instead of the annular form (not shown).

In a correction procedure, the open ends 53 of the fixing elements 43 can be reached cranially or caudally and be spread apart relative to one another using a tool not shown, in order to release an engagement with the clamping element 28, 29. This allows the second contact element 18 to be moved relative to the clamping elements 28, 29, for example to release the implant 90 from the spinous processes 12 and 14.

In the handling device 61, instead of the distal ends 74 and 75, a distal end 106 shown in portions in each case in FIG. 4B can also be used. The distal end 106 comprises a tongue 107, which, in particular, can approximately be the same size as the spacing of the clamping elements 28 and 29 from one another. Laterally next to the tongue 107, the distal end 106 has concave recesses 108, in which the clamping elements 28 and 29 can be positioned to allow a good relative orientation of the distal end 106 with respect thereto.

The implants 10 and 90 may be so-called "spacerless" implants, in which no spacer element present in the intervertebral space 30 is provided, in particular to support the spinous processes 12 and 14.

Figure 13:
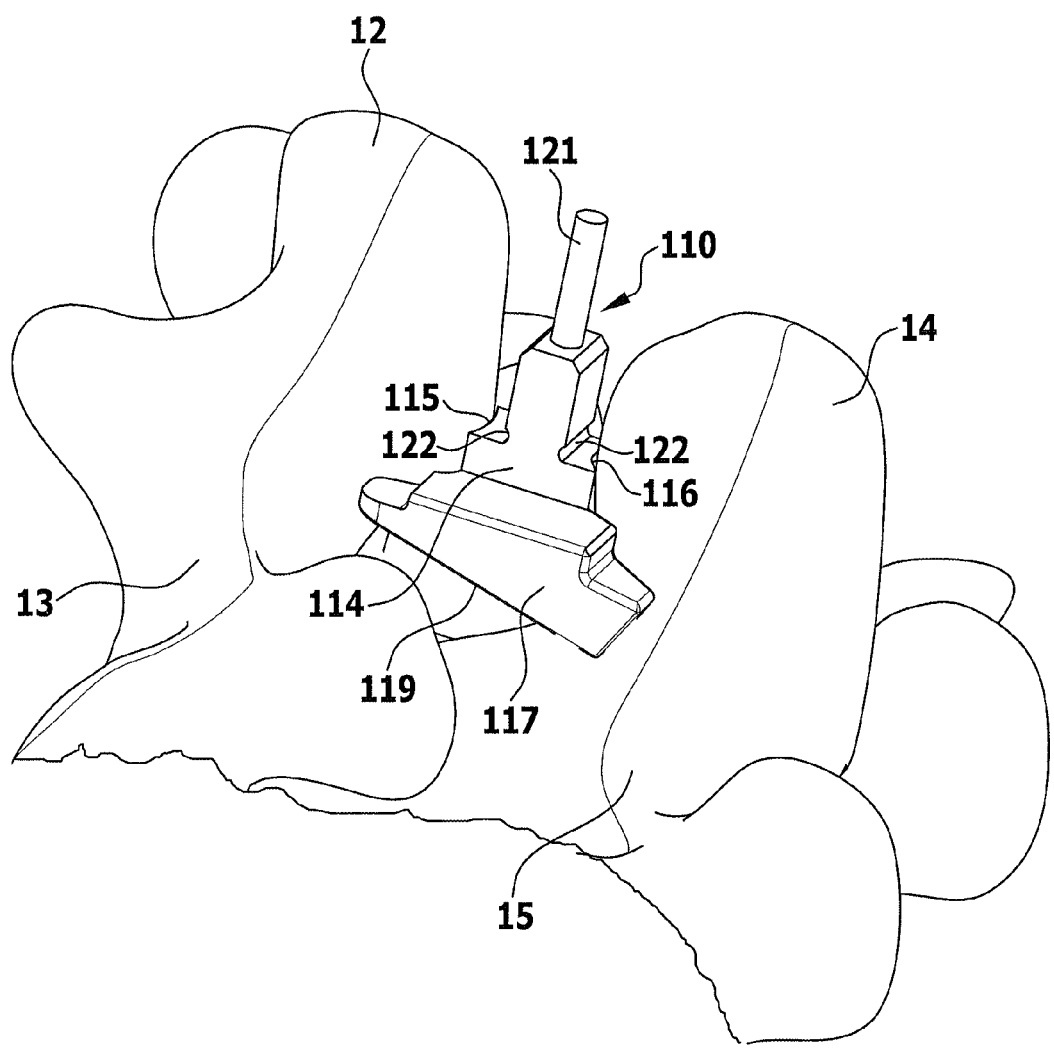
FIG. 13: shows a spacer element, which is arranged in the intervertebral space between spinous processes to be stabilized relative to one another and which can be used with the implant from FIG. 1 or FIG. 10, in a perspective view.
Figure 14:
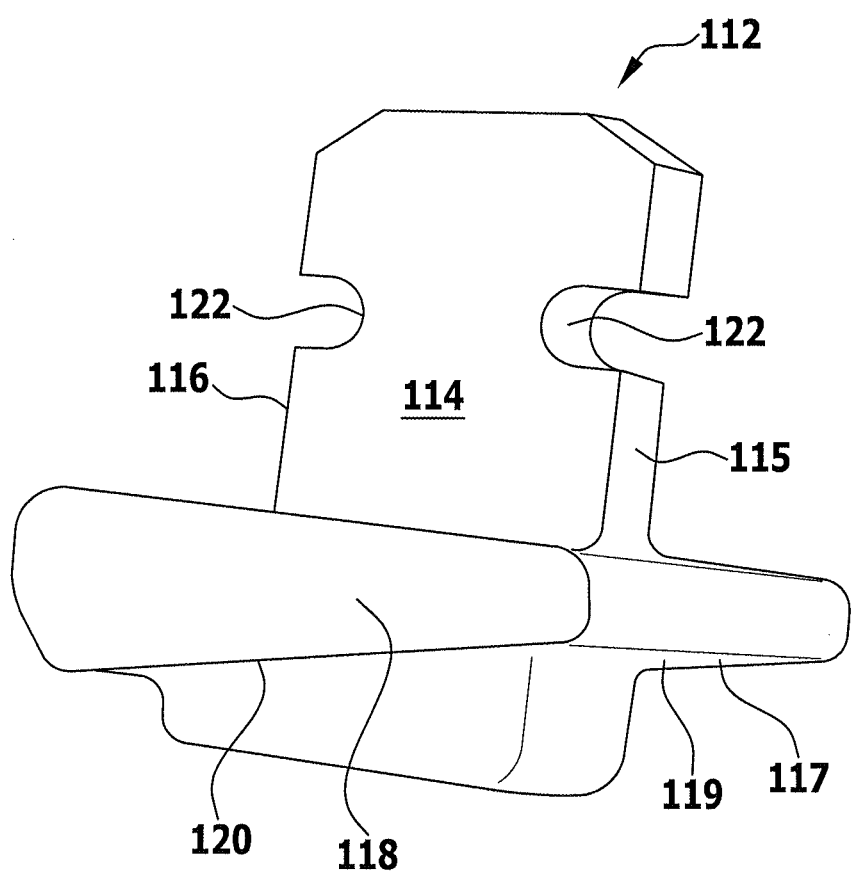
FIG. 14: shows a perspective view of a further spacer element, which can be used with the implant from FIG. 1 or FIG. 10.

However, the implants 10 and 90 may also be implants with a spacer element and, for example, comprise one of the spacer elements 110 or 112 shown in FIG. 13 or 14. From the functional point of view, the spacer elements 110 and 112 are substantially identical, so features that are the same, or which have the same effect, have the same reference numerals and the spacer element 110 will firstly be dealt with, in particular.

The spacer element 110 is formed in one piece and, for example, produced from a plastics material, in particular PEEK. It comprises a central portion 114, which can be positioned in the intervertebral space 30 and comprises a cranial contact face 115 for the spinous process 12 and a caudal contact face 116 for the spinous process 14. The contact faces 115 and 116 are, for example, groove-shaped.

Wing-like lateral portions project laterally on the anterior side from the central portion 114, of which lateral portions only one lateral portion 117 is shown in FIG. 13. A corresponding lateral portion, configured mirror symmetrically thereto, of the spacer element 110 is not shown in FIG. 13. The lateral portion 117 and the lateral portion 118 opposing it are shown in FIG. 14 using the example of the spacer element 112.

The portions 117 and 118 in each case form stop faces 119 or 120 on the anterior side for abutment of the spacer elements 110 and 112 on the laminae arcus vertebrae of the vertebral bodies 13 and 15. This allows a support of the spacer elements 110 and 112 to the anterior side and prevents their displacement into the spinal channel. An additional stabilization of the vertebral bodies 13 and 15 relative to one another is also made possible.

The spacer element 110 has a projection 121 on the posterior side, which can couple with a tool, not shown in the drawings, so that the spacer element 110 can be inserted in the intervertebral space 30. The tool can be released from the projection 121 and the projection 121 can be separated from the central portion 114.

Moreover, the spacer element 110 has recesses 122 on the central portion 114, in which the clamping elements 28 and 29 can engage. This allows the spacer element 110 to be brought into engagement with the rest of the implants 10 and 90 to allow an additional fixing in the intervertebral space 30. In particular, the rest of the implants 10 and 90 can be pushed in the dorso-ventral direction over the spacer element 110, because the central portion 114 has a taper on the posterior side and a spacing is therefore formed between the latter and the spinous processes 12 and 14.

The spacer element 112 is not provided with a projection 121, but recesses 122 are also present, through which the clamping elements 28 and 29 can extend. The spacer element 112 is inserted preassembled with the rest of the implants 10 and 90 in the intervertebral space 30, as the recesses 122 are also limited on the posterior side by the central portion 114. It is therefore not provided in the spacer element 112 that the rest of the implants 10 and 90 be slipped over the spacer element 112 in the dorso-ventral direction.

It may moreover be provided that the spacer elements 110 and 112 can be fixed in the intervertebral space 30 in particular by clamping or latching engagement with the contact elements 16 and 18.

What is claimed:

1. An implant for stabilizing spinous processes of adjacent vertebral bodies relative to one another, the implant comprising:
   A) a first contact element and a second contact element, wherein to stabilize the spinous processes, the first contact element can be placed laterally onto a first side of the spinous processes and the second contact element can be placed laterally onto a second side of the spinous processes, which is remote from the first side;
   B) at least one clamping element, coupling to the first contact element, and movable relative to the second contact element, the clamping element configured to extend through the intervertebral space between the spinous processes and extending through a through-hole formed in the second contact element, the through-hole having a length, with the clamping element passing completely through and projecting beyond the through-hole;
   C) at least one fixing element, which is arranged on the second contact element and which can be brought into engagement with the at least one clamping element to clamp the second contact element in the direction of the first contact element along the at least one clamping element; and
   D) an articulation device, by means of which at least one of the first contact element and the second contact element is arranged so as to be movable by tilting on the at least one clamping element,
   wherein:
   the first contact element is movable relative to the at least one clamping element in the longitudinal direction thereof;
   the at least one clamping element comprises at least one support member for support directly or indirectly on the first contact element against a movement in the direction of the second contact element;
   the articulation device comprises at least one articulation element through which the at least one clamping element extends, said articulation element having an articulation face, which cooperates with a corresponding articulation face of the first contact element facing away from the second contact element or a corresponding articulation face of the second contact element facing away from the first contact element; and
   the at least one articulation element comprises or forms an articulation sleeve, the at least one clamping element being displaceably guided in its longitudinal direction through the articulation sleeve.

2. The implant in accordance with claim 1, wherein the at least one fixing element can be brought into engagement with the at least one clamping element in at least one of a latching and a clamping manner and comprises fixing members, which, when the engagement exists, abut the at least one clamping element and allow a movement of the fixing element only in the direction of the first contact element.

3. The implant in accordance with claim 1, wherein the at least one fixing element is arranged on a side of the second contact element remote from the first contact element.

4. The implant in accordance with claim 1, wherein the implant has at least one fixing element receptacle, which is arranged on a side of the second contact element remote from the first contact element and in which the at least one fixing element is positionable, which fixing element receptacle has a first blocking member for the at least one fixing element to block its movement in the direction away from the second contact element and comprises a contact member to absorb a force directed onto the second contact element.

5. The implant in accordance with claim 4, wherein the at least one fixing element receptacle comprises a receptacle opening for at least one of an introduction of the at least one fixing element into the fixing element receptacle and a removal of the at least one fixing element from the fixing element receptacle.

6. The implant in accordance with claim 1, wherein the implant comprises two clamping elements arranged at a spacing with respect to one another and running parallel to one another.

7. The implant in accordance with claim 6, wherein the two clamping elements on the side of the second contact element remote from the first contact element are connected to one another by a bridge, which is supported on the clamping elements in the direction away from the second contact element.

8. The implant in accordance with claim 1, wherein the at least one articulation element is arranged on the first contact element.

9. The implant in accordance with claim 1, wherein the at least one articulation element is arranged on the second contact element.

10. The implant in accordance with claim 9, wherein the implant has at least one fixing element receptacle which is arranged on a side of the second contact element remote from the first contact element and in which the at least one fixing element is positionable, which fixing element receptacle has a first blocking member for the at least one fixing element to block its movement in the direction away from the second contact element and comprises a contact member to absorb a force directed onto the second contact element and wherein the at least one articulation element arranged on the second contact element comprises or forms the at least one fixing element receptacle for the at least one fixing element.

11. The implant in accordance with claim 1, wherein the contact elements each comprise a central portion and end portions, which project from the central portion on its mutually opposing sides along a first spatial direction and which are arranged offset relative to one another on the central portion in a second spatial direction transverse to the first spatial direction.

12. The implant in accordance with claim 11, wherein the contact elements in the transition region from the central portion to the end portions comprise or form deformation regions.

13. The implant in accordance with claim 1, wherein the contact elements comprise engagement members for engaging in the spinous processes, which project in the direction of the respective other contact element.

14. The implant in accordance with claim 13, wherein the contact elements each comprise a central portion and end portions which project from the central portion on its mutually opposing sides along a first spatial direction and which are arranged offset relative to one another on the central portion in a second spatial direction transverse to the first spatial direction, and wherein the engagement members are arranged on the end portions of the contact elements and wherein the central portions of the contact elements are free, or substantially free, of engagement members.

15. The implant in accordance with claim 13, wherein the engagement members of the first contact element and of the second contact element are staggered relative to one another.

16. The implant in accordance with claim 1, wherein the implant comprises at least one spacer element, which can be positioned in the intervertebral space and can be fixed by means of the rest of the implant.

17. The implant in accordance with claim 1, wherein the implant is an implant, which is free of spacer elements.

* * * * *